US008969516B2

(12) United States Patent
Bal et al.

(10) Patent No.: US 8,969,516 B2
(45) Date of Patent: Mar. 3, 2015

(54) METHOD OF HYDROLYSIS OF PEPTIDE BOND

(75) Inventors: Wojciech Bal, Mysiadlo p. Piaseczno (PL); Edyta Kopera, Mielec (PL); Artur Krezel, Wroclaw (PL); Aleksandra Wyslouch-Cieszynska, Wroclaw (PL)

(73) Assignee: Instytut Biochemii I Biofizyki Pan, Warsaw (PL)

( * ) Notice: Subject to any disclaimer, the term of this patent is extended or adjusted under 35 U.S.C. 154(b) by 1571 days.

(21) Appl. No.: 12/223,851

(22) PCT Filed: May 4, 2006

(86) PCT No.: PCT/PL2006/000026
§ 371 (c)(1),
(2), (4) Date: Jun. 22, 2010

(87) PCT Pub. No.: WO2007/091907
PCT Pub. Date: Aug. 16, 2007

(65) Prior Publication Data
US 2010/0256335 A1     Oct. 7, 2010

(30) Foreign Application Priority Data

Feb. 9, 2006 (PL) .......................................... 378946

(51) Int. Cl.
*C07K 1/02* (2006.01)
*C07F 15/04* (2006.01)

(52) U.S. Cl.
USPC ............................ 530/333; 530/343; 556/138

(58) Field of Classification Search
USPC ................................. 530/333, 343; 556/138
IPC .............. C07F 15/025; C07C 2523/755; C07K 1/00, 1/107, 1/12
See application file for complete search history.

(56) References Cited

U.S. PATENT DOCUMENTS

| 5,352,771 | A | 10/1994 | Kostic et al. |
| 6,933,362 | B1 | 8/2005 | Belfort et al. |
| 2005/0158838 | A1 | 7/2005 | Ley et al. |
| 2007/0134757 | A1* | 6/2007 | Linder et al. .................. 435/68.1 |

FOREIGN PATENT DOCUMENTS

| EP | 0134070 | A2 | 3/1985 |
| EP | 0161937 | A2 | 11/1985 |
| EP | 0288272 | A2 | 10/1988 |
| EP | 0339217 | A2 | 11/1989 |
| EP | 0505921 | A2 | 3/1992 |
| WO | 9410318 | A1 | 5/1994 |
| WO | 9416083 | A1 | 7/1994 |
| WO | 9502815 | A1 | 1/1995 |
| WO | 0032795 | A1 | 6/2000 |
| WO | 2005005458 | A1 | 1/2005 |
| WO | 2005007693 | A1 | 1/2005 |

OTHER PUBLICATIONS

Humphreys (Protein Engineering 13(3), 201-206, 2000).*
Yashiro et al. Metal-ion-assisted hydrolysis of dipeptides involving a serine residue in a neutral aqueous solution, Org. Biomol. Chem., 2003, 1, pp. 629-632.
Hirata et al. J. Biol. Chem. 1990, 265, 6726- 6733 "Molecular Structure of a Gene, VMA1, Encoding the Catalytic Subunit of H+-Translocating Adenosine Triphosphatase from Vacuolar Membranes of *Saccharomyces cerevisiae*".
Muir, Annu. Rev. Biochem. 2003, 72, 249-289 "Semisynthesis of Proteins by Expressed Protein Ligation".
Rana et al., J. Am. Chem. Soc. 1990, 112, 2457-2458 "Specific Cleavage of a Protein by an Attached Iron Chelate".
Sayre et al., Inorg. Chem. 1992, 31, 935-937 "Metal Ion Catalysis of Amide Hydrolysis. Very Large Rate Enhancements by Copper (II) in the Hydrolysis of Simple Ligand- Functionalized Tertiary Amides".
Fujii et al., J. Biol. Inorg. Chem. 2002, 7, 843-851 "Copper (II)-cis, cis-1, 3, 5-triaminocyclohexane Complex-promoted hydrolysis of dipeptides: kinetic, speciation and structural studies".
Kassai et al., Inorg. Chem. 2004, 43, 6130-6132 "Unprecedented Acceleration of Zirconium (IV)—Assisted Peptide Hydrolysis at Neutral pH".
Smith et al., Int. J. Peptide Protein Res. 1996, 48, 48-55 "Specific cleavage of immunoglobulin G by copper ions".
Zhang et al., Inorg. Chem., 2003, 42, 492-498 "Regioselective Cleavage of Myoglobin with Copper (II) Compounds at Neutral pH".
Hegg and Burstyn, J. Am Chem. Soc. 1995, 117, 70115-7016 "Hydrolysis of Unactivated Peptide Bonds by a Macrocyclic Copper (II) Complex: Cu([9]aneN3) Cl2 Hydrolyzes Both Dipeptides and Proteins".
de Oliveira et al., Inorg. Chem., 2005, 44, 921-929 "Hydrolytic Protein Cleavage Mediated by Unusual Mononuclear Copper (II) Complexes: X-ray Structures and Solution Studies".
Zhu et al., J. Biol. Inorg. Chem., 1998, 3, 383-391 "Transition-metal complexes as alternatives to proteolytic enzymes. Regioselective cleavage of myoglobin by palladium (II) aqua complexes".

(Continued)

*Primary Examiner* — David Lukton
(74) *Attorney, Agent, or Firm* — Brooks Kushman P.C.

(57) ABSTRACT

This invention relates to a method of hydrolysis of the peptide bond between $R_1$ and B in a specific designed amino acid sequence $R1BXJZR_3R_2$, where $R_1$ represents a polypeptide of interest, $R_2$ represents a sequence capable of specific binding to another component or molecule or another domain which needs to be cleaved, $R_3$ represents an optional short peptide sequence, B represents a residue capable of accepting an acyl group, J represents a residue capable of metal ion binding, and X and Z represent amino acid residues, wherein the said method is based on a novel molecular mechanism of peptide bond hydrolysis, occurring in a specific complex of this metal ion with the BXJZ sequence. This method can be used to remove $BXJZR_3R_2$ domains in recombinant polypeptides, such as sequences capable of specific binding to another component or molecule to yield pure, unmodified $R_1$ polypeptides of interest. The intermediate hydrolysis product can be reacted with other compounds to obtain derivatives of polypeptides of interest modified covalently at the C-terminus.

37 Claims, 5 Drawing Sheets

(56) References Cited

OTHER PUBLICATIONS

Figure 1:
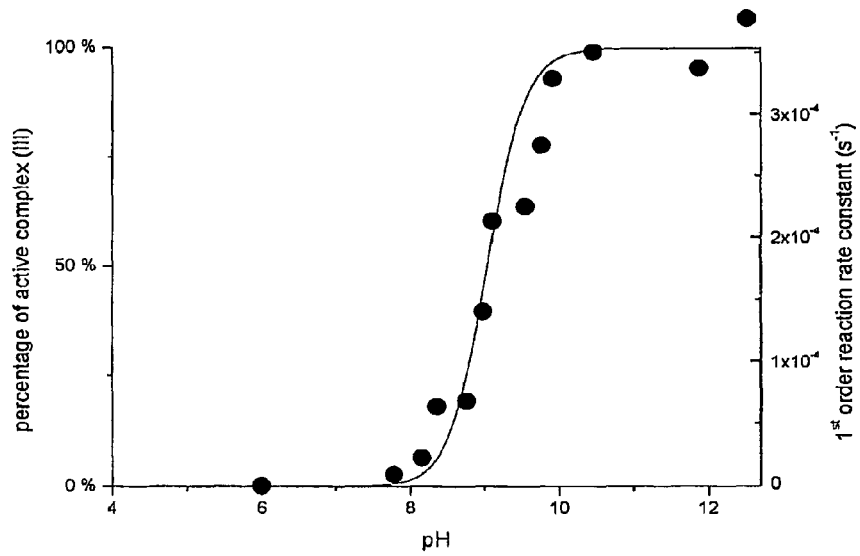

Milovic et al., J. Am. Chem. Soc. 2003, 125, 781-788 "Palladium (II) Complex as a Sequence-Specific Peptidase: Hydrolytic Cleavage under Mild Conditions of X-Pro Peptide Bonds in X-Pro-Met and X-Pro-His Segments".

Zhu and Kostic (Inorg. Chim. Acta 2002, 339, 104-110 "Sequence-dependent cleavage of albumins with palladium (II) complexes: role of serine residue in controlling the high regioselectivity of protein cleavage".

Manka et al., J. Inorg. Biochem. 2004, 98, 1947-1956 "Cisplatin-mediated selective hydrolytic cleavage of methionine-containing peptides with neighboring serine or histidine residues".

Dutca et al. (Inorg. Chem., 2005, 44, 5141-5146 "Platinum (II) Complex as in Artificial Peptidase: Selective Cleavage of Peptides and a Protein by cis-[Pt(en)(H20)2]2+ Ion under Ultraviolet and Microwave Irradiation".

Allen and Campbell, Int. J. Pept. Protein Res. 1996, 48, 265-273 "Specific cleavage of histidine-containing peptides by copper (II)".

Bal et al., Interactions of Nickel (II) with Histones: Interactions of Nickel (II) with CH3CO—Thr—Glu—Ser—His_His—Lys—NH2, a Peptide Modeling the Potential Metal Binding Site in the "C-Tail" Region of Histone H2A, Chem. Res. Toxicol., 1998, 11, pp. 1014-1023.

Bal et al., Chem. Res. Toxicol., 2000, 13, 616-624 "Ni (II) Specifically Cleaves the C-Terminal tail of the Major Variant of Histone H2A and Forms an Ocidative Damage-Mediating Complex with the Cleaved-Off Octapeptide".

Mylonas et al., J. Chem. Soc, Dalton Trans., 2002, 4296-4306 "The binding of Ni (II) ions to terminally bloakc hexapeptides derived from the metal binding —ESHH— motif of histone H2A".

Kozlowski et al., Coord. Chem. Rev. 1999, 184, 319-346 "Specific structure-stability relations in metallopeptides".

Sigel and Martin, Chem. Rev. 1982, 82, 385-420 "Coordinating Properties of the Amide Bond. Stability and Structure of Metal Ion Complexes of Peptides and Related Ligands".

Terpe, Appl. Microbiol. Biotechnol. 2003, 60, 523-533 "Overview of tag protein fusions: from molecular and biochemical fundamentals to commercial systems".

Bal and Kasprzak, Toxicol. Lett. 2002, 127, 55-62 "Induction of oxidative DNA damage by carcinogenic metals".

Carugo, In Silico Biol. 2003, 3, 0035 "Prediction of polypeptide fragments exposed to the solvent Oliviero Carugo".

Fields, Meth. Enzymol. vol. 289 "Methods in enzymology: Solid-Phase Peptide Synthesis".

Krezel et al., Chem. Res. Toxicol. 2003, 16, 855-864 "Correlations between Complexation Modes and Redox Activities of Ni (II)—GSH Complexes".

Sokolowska and Bal, J. Inorg. Biochem. 2005, 99, 1653-1660 "Cu(II) complexation by "non-coordinating" N-2-hydroxyethylpiperazine-N-2-ethanesulfonic acid (HEPES buffer)".

Jencks et al., J. Biol. Chem. 1960, 235, 3608-3614 "The Free Energy of Thiol Ester Hydrolysis".

Chavira et al., Anal. Biochem. 1984, 136, 446-450 "Assaying Proteinases with Azocoll".

Karaczyn et al., Chem. Res. Toxicol. 2003, 16, 1555-1559 "The Octapeptidic End of the C-Terminal Tail of Histone H2A is Cleaved off in Cells Exposed to Carcinogenic Nickel (II)".

Radzicka, A., Wolfenden, R., J. Am. Chem. Soc. 1996, 110, 6105-6109 "Rates of Uncatalyzed Peptide Bond Hydrolysis in Neutral Solution and the Transition State Affinities of Proteases".

European patent office International Search Report for PCT/PL2006/000026 and the Written Opinion dated Dec. 13, 2006.

English Abstract of CN 1371918A, published Oct. 2, 2002, supplied from esp@cenete database-Worldwide on Sep. 30, 2009, 1 pg.

English Abstract of JP 10045796A, published Feb. 17, 1998, supplied from esp@cenete database-Worldwide on Sep. 30, 2009, 1 pg.

* cited by examiner

Scheme I

Scheme II

METHOD OF HYDROLYSIS OF PEPTIDE BOND

This application is a 371 of PCT/PL2006/000026, filed May 4, 2006, which claims foreign priority to Polish application P.378946, filed Feb. 9, 2006.

This invention relates to a method of hydrolysis of the peptide bond between $R_1$ and B in a specific designed amino acid sequence $R_1BXJZR_3R_2$, where $R_1$ represents a polypeptide of interest, $R_2$ represents a sequence capable of specific binding to another component or molecule, or another domain which needs to be cleaved, and $R_3$ represents an optional short peptide sequence, wherein the said method is based on a novel molecular mechanism, occurring in a specific complex of this metal ion with the BXJZ sequence. This mechanism involves a metal ion assisted transfer of $R_1$ to the side chain of residue B, to form an intermediate product, which subsequently undergoes hydrolysis. This method can be used to remove C-terminal $BXJZR_3R_2$ domains in recombinant polypeptides, to yield pure, unmodified target $R_1$ polypeptides of interest. The intermediate product can also be reacted with other compounds to obtain derivatives of $R_1$ with the carboxyl group at its C terminus modified.

BACKGROUND OF THE INVENTION

The cleavage of the peptide bond is a subject of ongoing interest, being one of the most common and most important procedures in biochemistry. However, the extreme stability of this bond, with half-life for spontaneous hydrolysis estimated as 350-600 years at neutral pH and room temperature (Radzicka, A., Wolfenden, R., J. Am. Chem. Soc. 1996, 110, 6105-6109) limits the range of reagents for efficient peptide or protein cleavage. Proteolytic enzymes are natural reagents that cleave peptide bonds with various degrees of specificity. However, only a few of them are used routinely in industrial or laboratory practice, due to such limitations as their narrow requirements for temperature and pH. Therefore, new agents that provide the selective cleavage of peptides and proteins have gained increasing importance. Potential applications are foreseen in protein engineering. They include the removal of functional domains from recombinant polypeptides in protein purification procedures, processing of precursors of active proteins, etc.

Developments in recombinant DNA technology have made it possible to express a wide range of cloned foreign genes in host organisms such as bacteria and yeast. The usage of suitable recombinant polypeptides for the expression of peptides or proteins of interest has become a common practice. Such carriers have several advantages. They may be selected to increase solubility of proteins of interest, to prevent their degradation in host cells or to simplify purification and detection procedures. However, it is often necessary to remove the added functional partner from the polypeptide of interest by means of specific peptide bond cleavage. This concerns for example pharmaceutical applications, where foreign polypeptide sequences can elicit immune response in patients, or structural investigations. A suitable method of peptide bond cleavage must be both specific and efficient and must not yield unwanted side products. In particular, such a method should not introduce such modifications in the polypeptide of interest, which would be difficult to remove. Furthermore, for pharmaceutical or other life sciences applications, such a method should not pose a threat of contamination of the product with pathogens.

One common approach to the issue of specific peptide bond cleavage is to use proteolytic enzymes. The most frequently used ones include Factor Xa (for example Nagai et al., EP0161937 and Grandi et al., EP0505921), enterokinase (for example LaVallie, EP0679189 and Ley et al., US2005158838), and thrombin (for example Gilbert et al., EP0666920). However, several serious inconveniences accompany enzymatic proteolysis. These include non-specific proteolytic attack on the polypeptide of interest; a need for extended incubations, which can cause denaturation or aggregation of the polypeptide of interest; incomplete cleavage, which reduces the yield and/or introduces heterogeneity to the purified polypeptide; the need for additional purification steps to separate it from the fusion partner, deactivate and remove protease, and exchange buffer or salt. Finally, proteolytic enzymes are often expensive, and thus not feasible for the large-scale use in pharmaceutical, clinical and biotechnological applications.

Another family of methods for specific peptide bond cleavage is based on protein splicing with inteins, naturally occurring internal sequences, which undergo an intramolecular rearrangement, through the formation and subsequent hydrolysis of an active (thio)ester. The latter step leads to an elimination of the intein and recombination of the neighbouring sequences (Hiera et al. J. Biol. Chem. 1990, 265, 6726-6733). Recently a number of mutant inteins have been designed that are able to promote only the first step of protein splicing (Muir, Annu. Rev. Biochem. 2003, 72, 249-289). In this approach, the polypeptide of interest is fused to a self-cleavable intein domain, which can be cleaved alternatively via an intermolecular trans(thio)esterification reaction with external thiols, such as dithiotreitol, β-mercaptoethanol or cysteine. This increasingly popular methodology has several drawbacks. The cleavage reaction requires the addition of thiols that modify the C-terminus of the polypeptide of interest. It is strictly dependent on the preservation of native intein conformation, which results in specific narrowed requirements for reaction conditions. Also the large sizes of intein moieties constitute a disadvantage because they can diminish solubility and purification efficiency (Belfort et al. U.S. Pat. No. 6,933,362).

A further family of specific peptide bond cleavage methods is based on chemical cleavage agents. These often require harsh reaction conditions. Even when added at a great excess over the substrate, they tend to cleave only with partial selectivity and low yield. Cyanogen bromide is one of principal chemical reagents for peptide bond hydrolysis. Although used commonly, it has several serious shortcomings. It is volatile and very toxic, is applied at a 100-fold excess over methionine residues, for which it is specific, requires 70% formic acid as solvent, and gives several unwanted side reactions. As a consequence of its specificity for single methionine residues, for proteins with additional methionines cyanogen bromide produces protein fragments that are no longer native because methionine residues in them undergo irreversible modifications (Dimarchi, EP0134070). Another way of chemical cleavage is to react a protein or peptide with hydroxylamine, which cleaves the bond between the Asn and Gly residues. Disadvantages of this approach include side reactions of hydroxylamine with other Asn and Gly residues in a protein or peptide, yielding hydroxamates (Wang, CN1371918). The cleavage of an Asn-Gly bond in a protein or peptide was disclosed (Palm, WO952815), by treating it with a compound of the general formula $R_1$—$(CH_2)_n$—NH—$(CH_2)_m$—$R_2$, wherein $R_1$ denotes $NH_2$ or OH, $R_2$ denotes hydrogen, lower alkyl, $NH_2$, OH or halogen, n denotes an integer from 1 to 3, and m denotes 0 or an integer from 1 to 3. This is a generalisation of the hydroxylamine cleavage, possessing similar limitations. A chemical method for peptide bond cleavage at tryptophan residues was also disclosed (Richiyaado, EP0288272), by treating a peptide or protein with trifluoroacetic acid, in the presence of sulfoxide and chloride ions. Hinman et al. (EP0339217) disclosed the cleavage of peptide bonds by nucleophilic tertiary organophosphines. Another method includes the peptide bond cleavage between a Lys and a Cys residue. In this reaction the cysteine residue is first cyanogenated, then the peptide is treated with weak alkali and the amino group of the lysine acts as a nucleophilic group attacking the carbonyl carbon on the peptide bond between Lys and the cyanocysteine residue and cleaving this bond (Iwakura et al., JP10045796). The use of the chemical cleavage methods outlined above will in most cases generate non-specific protein fragmentation, since tryptophan residues, and Asn-Gly or Lys-Cys pairs are frequently found in proteins. Another serious disadvantage of these methods is the use of toxic or harmful chemicals.

Various metal ions, including $Cu^{2+}$, $Zn^{2+}$, $Pt^{2+}$, $Pd^{2+}$, $Ni^{2+}$, $Cd^{2+}$, $Fe^{2+}$, $Fe^{3+}$, $Ce^{3+}$, $Eu^{3+}$ and $Pr^{3+}$ were studied as agents for non-enzymatic peptide bond cleavage—uncomplexed or complexed with specific ligands; the latter are often called artificial metallopeptidases. Two general cleavage mechanisms can be employed. Redox reactions of metal ion chelates, were studied, often in the presence of $H_2O_2$/ascorbate (for example, see Rana et al., J. Am. Chem. Soc. 1990, 112, 2457-2458). According to Linder et al. (WO2005005458) an amino acid sequence, comprising at least two amino acids selected from the group comprising histidine, lysine, tryptophan, arginine, tyrosine, phenylalanine and cysteine is constructed at the predetermined cleavage site and proteins or peptides are allowed to react with free metal ions in the buffer. The buffer contains a reducing or oxidizing agent which enhances the cleavage. In fact, redox cleavage of oligo-His and oligo-His-X sequences by $Cu^{2+}$ and $Co^{2+}$ ions was demonstrated only by gel electrophoresis, without a further analysis of cleavage products, and therefore the accuracy of cleavage by this reaction remains to be demonstrated. As with other redox reactions of metal ions, multiple side-reactions of free radical character should be expected, for example side chain oxidations.

An alternative chemistry, based upon hydrolysis reactions, is employed in the majority of other approaches. Suh and Son (EP 1381392) disclosed a family of synthetic catalysts of general formula $(R)(Z)_n$, in which n denotes an integer of 1 or more, R represents a material capable of selectively recognizing and binding a target protein and Z represents an active metal ion-ligand complex. The cleavage was proved for $Cu^{2+}$ and $Co^{3+}$ complexes, using myoglobin and avidin as protein substrates, but sequence specificity was low. This methodology requires R to be designed individually for each substrate and cleavage site, and the synthesis of appropriate catalysts is laborious.

Many studies were made on model systems such as activated amides (Sayre et al., Inorg. Chem. 1992, 31, 935-937 and references therein) and dipeptides or small peptides (Fujii et al., J. Biol. Inorg. Chem. 2002, 7, 843-851 and references therein, Kassai et al., Inorg. Chem. 2004, 43, 6130-6132 and references therein), but the hydrolytic cleavage of proteins was achieved only in several cases. Smith et al. showed that $Cu^{2+}$ ions, and also $Ni^{2+}$, $Zn^{2+}$, $Mn^{2+}$, $Mg^{2+}$, $Ca^{2+}$, $Fe^{2+}$ ions were able to cleave (with various efficacies) the $Lys_{226}$-$Thr_{227}$ peptide bond in the hinge region of human $IgG_1$ but did not propose a molecular mechanism (Smith et al., Int. J. Peptide Protein Res. 1996, 48, 48-55). The scission of myoglobin with low sequence specificity was proved for a series of $Cu^{2+}$ compounds (Zhang et al., Inorg. Chem., 2003, 42, 492) which exhibited two adjacent cleavage sites. Another study on BSA, using a macrocyclic $Cu^{2+}$ complex, demonstrated several preferred sites of cleavage, but no clear sequence specificity could be observed (Hegg and Burstyn, J. Am. Chem. Soc. 1995, 117, 70115-7016). Although in some cases the protein cleavage may be rapid, the sequence specificity of such reactions is still poor and hard to predict (de Oliveira et al., Inorg. Chem., 2005, 44, 921-929).

Yashiro et al. studied the mechanism of hydrolysis of peptides containing Ser residues, with a low sequence specificity, defined as -Xaa-Ser-, where Xaa denotes any amino acid. The mechanism of this reaction consists of an acyl shift, with a possible role for $Zn^{2+}$, $Cu^{2+}$, $Ni^{2+}$, $Pr^{3+}$ or $Eu^{3+}$ added as free ions or complex species to polarize the peptide carbonyl group by coordination, and to promote the nucleophilic attack of an intramolecular OH group (Yashiro et al., Org. Biomol. Chem., 2003, 1, 629-632 and references therein).

A different mechanism was proposed for hydrolytic reactions mediated by $Pt^{2+}$ and $Pd^{2+}$ complexes. Kostic and Zhu (U.S. Pat. No. 5,352,771) disclosed complexes of $Pt^{2+}$ and $Pd^{2+}$ which selectively bind to sulfur atoms in side chains of residues such as methionine, cysteine and S-alkyl cysteine and promote the cleavage of peptide bonds adjacent to these sulfur-containing residues. The disclosed mechanism of this process assumes that either an internal transfer of a water molecule from the metal complex to the amide group or the attack of the exogenous water molecule derived from the aqueous reaction medium on the amide group is the crucial step of this reaction. Although these inventors proposed a wide variety of peptides and proteins which could be hydrolysed with this method (e.g. myoglobin, Zhu et al., J. Biol. Inorg. Chem., 1998, 3, 383-391), the low pH of the reaction, around 2, together with a low sequential specificity, limit the range of applications. A similar peptide bond cleavage mechanism between X and Z residues was also demonstrated for a $Pd^{2+}$ complex and peptides of X-Z-His sequences (Milovic et al., J. Am. Chem. Soc. 2003, 125, 781-788 and references therein). This methodology is well suited for protein fragmentation for mass spectroscopy. Yet another mechanism was proposed speculatively by Zhu and Kostic (Inorg. Chim. Acta 2002, 339, 104-110) for the cleavage of Ser/Thr-His/Met sequences in human serum albumin (HSA) by $Pd^{2+}$ complexes. It includes an acyl group shift with the formation of an intermediate ester with the alcoholic group present in the Ser/Thr side chain. This mechanism was cited for the cisplatin-mediated selective hydrolytic cleavage of acetic acid from the Ac-Ser-Met dipeptide, but not for the reaction of the Ac-Ser-His dipeptide (Manka et al., J. Inorg. Biochem. 2004, 98, 1947-1956).

Recently, Dutca et al. (Inorg. Chem., 2005, 44, 5141-5146) reported enhanced cleavage of Met-X peptide bonds by a $Pt^{2+}$ complex under ultraviolet or microwave irradiation.

Humphreys (WO0032795) proposed the cleavage sites comprising the -DKTH-, -DRSH-, -EKSH- or -DKSH- sequences which are specifically cleaved by $Cu^{2+}$ ions at temperatures above 50° C. However, the $Cu^{2+}$ related hydrolysis was demonstrated previously to occur simply for Ser-His and Thr-His sequences under such conditions (Allen and Campbell, Int. J. Pept. Protein Res. 1996, 48, 265-273) and therefore multiple unspecific cleavages should be expected for this method.

Altogether then, the reactions of metal ions proposed previously and presented above share a disadvantage of low sequence specificity, based on one or two adjacent amino acid residues. Therefore they are suited better for protein fragmentation than for selective cleavage of dedicated sites that would occur without side reactions.

The Ac-TESHHK-NH$_2$ hexapeptide was recently found to undergo a slow, spontaneous, sequence-specific hydrolysis in the presence of Ni$^{2+}$ ions in a phosphate buffer, at pH 7.4 and 37° C. (Bal et al., Chem. Res. Toxicol., 1998, 11, 1014-1023). A Ni$^{2+}$ complex of the C-terminal tetrapeptide amide SHHK-NH$_2$ was found to be the product of this reaction, with a yield between 3% and 9% after 140 hours of incubation, depending on the concentration of Ni$^{2+}$ ions. The cleavage occurred therefore between the Glu and Ser residues. Subsequent studies revealed that a peptide of 34 residues, comprising the above sequence, was cleaved with an identical sequence specificity by Ni$^{2+}$ ions under analogous conditions, but ca. five times faster (Bal et al., Chem. Res. Toxicol., 2000, 13, 616-624). The same work demonstrated that Cu$^{2+}$ ions hydrolysed this 34-peptide with the same specificity, but slower. The other two metal ions tested, Co$^{2+}$ and Zn$^{2+}$ were inactive. An analogous hydrolysis reaction was also seen for Ni$^{2+}$ ions and histone H2A, which was the source of the hexapeptide and 34-peptide sequences. Further studies on Ala-substituted hexapeptide analogues of Ac-TESHHK-NH$_2$ indicated that the reaction proceeded at alkaline pH, and allowed to identify the Ser residue and the C-terminal H is residue as the ones necessary for it to occur. The substitution of the Glu residue with Ala did not affect the reaction (Mylonas et al., J. Chem. Soc., Dalton Trans., 2002, 4296-4306). This published research indicated that peptides which could potentially be hydrolysed under alkaline conditions in the presence of metal ions, such as Ni$^{2+}$, are represented by a general sequence P$_1$SA$_1$HP$_2$, where P$_1$ and P$_2$ represent any peptide sequences, and A$_1$ represents any amino acid residue.

The above description clearly demonstrates that there is a need for a method of selective cleavage of a peptide bond in a peptide or a protein, which would combine advantages of chemical agents, such as low cost and easy removal of the cleaving agent, with advantages normally associated with enzymatic reactions, such as high sequence specificity and reproducibility of cleavage and a lack of side reactions.

The present invention provides such a method, based on a novel molecular mechanism involving metal ions.

DESCRIPTION OF THE INVENTION

The method of hydrolysis of the peptide bond between the peptide sequence R$_1$ and the amino acid residue B consists in designing and obtaining by molecular biology methods, in particular by overexpression, a recombinant polypeptide represented by the general formula R$_1$BXJZR$_3$R$_2$, which contains, starting from N-terminus: an amino acid sequence of polypeptide of interest R$_1$, a metal cation binding sequence BXJZ, and a functional domain R$_3$R$_2$, wherein:

R$_1$ denotes the sequence of the polypeptide to be obtained, preferably the polypeptide of interest to be purified, which contains a C-terminal amino acid residue capable of forming a peptide bond with the amino acid residue B.

R$_2$ denotes the sequence of the peptide or protein which is being removed, preferably the sequence capable of specific binding to another component or molecule.

R$_3$ denotes the sequence of the peptide or protein, preferably an oligopeptide spacer sequence, which separates R$_2$ from other parts of the recombinant protein, preferably Ala-Pro sequence.

B denotes an amino acid residue, whose —NH— group participates in the peptide bond together with the terminal amino acid residue of R$_1$ sequence, which is represented by the general formula 1, where R$_{11}$, R$_{12}$, R$_{13}$ denote independently a hydrogen atom, an alkyl or hydroxyalkyl group of 1 to 15 carbon atoms or a hydroxyl group, and Y$_B$ denotes a hydroxyl, thiol or selenol group capable of substituting for the nitrogen atom and forming a chemical bond with the C-terminal carbon atom of R$_1$, and thereby reacting as an acceptor of the acyl group derived from R$_1$.

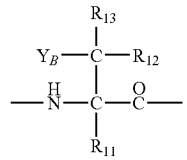

formula 1

X denotes an amino acid residue, occurring naturally or synthetic, containing an —NH— group, which forms a peptide bond of a —C(O)—NH— type together with the amino acid residue B.

J denotes an amino acid residue, occurring naturally or synthetic, containing the —NH— group, which forms a peptide bond of a —C(O)—NH— type together with amino acid residue X and contains in its side chain a Y$_J$ group capable of forming a chemical bond with a metal ion, selected from the group comprising inorganic acid residues, such as sulfate, nitrate or phosphate, organic acid residues, such as carboxylates, phenols, amines, such as primary, secondary or tertiary aliphatic or alicyclic amines, phosphines, thiols, thioeters, heterocycles, such as derivatives of pyridine, imidazole, trains.

Z denotes an amino acid residue, occurring naturally or synthetic, containing the —NH— group, which forms a peptide bond of the —C(O)—NH— type together with amino acid residue J;

and, having used the recombinant polypeptide constructed in this way for its planned purpose, the polypeptide of interest R$_1$ is cleaved off by contacting it with a metal ion M$^{n+}$ selected from the group comprising Cu$^{2+}$, Cu$^{3+}$, Pt$^{2+}$, Pt$^{4+}$, Pd$^{2+}$, Au$^{3+}$, Ag$^{2+}$, Ni$^{2+}$, Ni$^{3+}$, and other di-, tri- or tetravalent metal ions, capable of forming bonds simultaneously with group and main chain peptide nitrogen atoms of residues J, X and B, in a buffered solution, preferably Tris or Hepes, until completion of the process of hydrolysis of the peptide bond between R$_1$ and B.

In the method according to the invention the preferred operation for which the functional domain R$_3$R$_2$ is created consists of contacting the recombinant protein, being present in the mixture of biological origin, preferably a cellular lysate or homogenate, with a compound immobilized on a solid support which is capable of interacting specifically with R$_3$R$_2$, followed by washing off other compounds present in the biological mixture.

In the method according to the invention, the actual reaction of peptide bond hydrolysis is performed preferably following the removal of the recombinant protein from the solid support, or directly on the solid support, wherein the products are separated using standard techniques when the procedure is performed in solution, while pure R$_1$ polypeptide in solution is obtained following the peptide bond hydrolysis on the solid support.

In the method according to the invention, the amino acid residue X preferably contains a side chain denoted R$_x$ in Schemes I and II, which is characterized with a large van der Waals volume.

In the method according to the invention, the amino acid residue Z preferably contains a side chain, denoted R$_z$ in Schemes I and II, which is characterized with a high hydrophobicity.

In the method according to the invention, preferably the amino acid residue X is characterized with a large van der Waals volume and the amino acid residue Z is characterized with a high hydrophobicity.

In the method according to the invention, the peptide sequence preferably contains an optional peptide sequence $R_3$.

In the method according to the invention, the $R_3$ peptide sequence preferably contains one, two or more amino acid residues, which separate the $R_2$ peptide sequence from the BXJZ sequence, preventing an interference with the action specific to the $R_2$ peptide sequence.

In the method according to the invention, the $R_3$ peptide sequence, preferably contains one, two or more amino acid residues, which separate the $R_2$ peptide sequence from the BXJZ sequence, preventing the inhibition of binding of metal ions according to the invention to the BXJZ peptide sequence.

In the method according to the invention the $R_2$ peptide sequence preferably denotes a peptide or protein which is capable of specific binding to or interacting otherwise with another component or molecule.

In the method according to the invention amino acid residues B, X, J and Z are preferably synthetic or occur naturally, including natural amino acid residues which were modified posttranslationally.

In the method according to the invention the amino acid residue J is preferably selected from the group comprising amino acid residues Asp, Glu, Tyr, Met, Cys, His.

In the method according to the invention the amino acid residue J is preferably selected from the group comprising amino acid residues Cys and His:

In the method according to the invention the amino acid residue H is is used preferably for the amino acid residue J.

In the method according to the invention the amino acid residue B is preferably selected from the group comprising amino acid residues Ser, Thr, Cys.

In the method according to the invention, amino acid residue B is preferably selected from the group comprising amino acid residues Ser and Thr.

In the method according to the invention the amino acid residue Ser is used preferably for the amino acid residue B.

In the method according to the invention the amino acid residue X is preferably selected from the group comprising amino acid residues Met, Phe, Lys, Trp, Arg.

In the method according to the invention the amino acid residue X is preferably selected from the group comprising amino acid residues Lys, Trp, Arg.

In the method according to the invention the amino acid residue Arg is used preferably for the amino acid residue X.

In the method according to the invention the amino acid residue Z is preferably selected from the group comprising amino acid residues Lys, Val, Arg, Ile, Leu, Trp.

In the method according to the invention the amino acid residue Trp is used preferably for the amino acid residue Z.

In the method according to the invention the reaction environment preferably contains components which do not bind metal ions, except for the recombinant protein $R_1BXJZR_3R_2$ being cleaved and products of its hydrolysis.

In the method according to the invention the water solutions of Tris or Hepes buffers are preferred hydrolysis environments.

In the method according to the invention the hydrolysis environment preferably contains one or more components which accelerate hydrolysis of the chemical bond between the $Y_B$ group and the C-terminal carbon atom of the $R_1$ polypeptide sequence, selected from the group comprising natural and synthetic esterases and thioesterases.

In the method according to the invention the hydrolysis environment preferably contains one or more components which form covalent bonds with the C-terminal carbon atom of the $R_1$ polypeptide, selected from the group comprising hydroxylamine and its derivatives, alcohols, phenols, thiols, amines, phosphines and other compounds having similar properties.

The metal ion is preferably selected from the group comprising $Cu^{2+}$, $Pt^{2+}$, $Pd^{2+}$, $Ni^{2+}$ in the method according to the invention.

The metal ion is preferably selected from the group comprising $Cu^{2+}$ and $Ni^{2+}$ in the method according to the invention.

$Ni^{2+}$ is the preferred metal ion in the method according to the invention.

All one letter symbols describe individual amino acid residues, according to the official IUPAC nomenclature, unless defined otherwise above. Three letter amino acid symbols are also used according to this nomenclature.

In the method according to the invention it was surprisingly found that certain specific substitutions in positions B, X, J and Z of the general sequence $R_1BXJZR_3R_2$ result in a dramatic increase of the rate of hydrolysis of the peptide bond preceding the B residue, dependent on metal ion $M^{n+}$, while preserving the sequence specificity of the reaction. The choice of these preferred substitutions is based on experimental data, presented in the examples attached below, as well as on consequent theoretical considerations making it possible to elucidate the general molecular mechanism responsible for this hydrolysis reaction. Advantageous features of optimized $R_1BXJZR_3R_2$ sequences make the said reaction suitable as a method of hydrolysis of peptide bond in a variety of applications, preferably including, but not limited to the cleavage of functional domains from polypeptides of interest.

The molecular mechanism of the peptide bond hydrolysis, which provides novelty of the present invention, consists of five principal steps, shown in Scheme 1.

In step 1 the metal ion $M^{n+}$ spontaneously forms a bond to the $Y_J$ group of the J residue in the $R_1BXJZR_3R_2$ sequence. In step 2 the metal ion $M^{n+}$ forms additional coordination bonds to amide nitrogens of residues J, X, and B (complex III). This occurs in a stepwise, pH-dependent fashion, because hydrogen ions have to be displaced from these nitrogen atoms by $M^{n+}$. As a result, relative concentrations of complexes containing one (J), then two (J and X) and finally three (J, X and B) $M^{n+}$-peptidic nitrogen bonds increase at higher pH values. The equilibrium is established in minutes to hours, depending on the peptide sequence, temperature and pH. Steps 1 and 2 are common to all sequences containing single J residues. Additional complex forms may exist with peptides in which residues X and/or Z or other residues share properties with J residue, that is they are able to coordinate metal ions through their side chains, but complex (III) will always be present as a major species at a sufficiently high pH. The reactions of steps 1 and 2 are well known to those skilled in the art, and were described for many examples (see for example Kozlowski et al., Coord. Chem. Rev. 1999, 184, 319-346, Sigel and Martin, Chem. Rev. 1982, 82, 385-420). An attack of the group $Y_B$ on the $R_1$—B peptide bond follows in step 3. The participation of $Y_B$ in the hydrolysis reaction was suggested in the literature cited above, for B denoting a Ser or Thr residue. A novel and unexpected aspect of step 3 is that for the amino acid sequence $R_1BXJZR_3R_2$ the attack of the group $Y_B$ on the $R_1$—B peptide bond occurs specifically in complex (III), in which $M^{n+}$ is coordinated to $Y_J$ and three peptide nitrogen atoms of residues J, X, and B. This fact is demonstrated by the pH profile of hydrolysis, presented in Example 3 below for J denoting His. In a consequence, step 4 consists of the intramolecular transfer of $R_1$ acyl group from the amino group of residue B to the group $Y_B$, to form an active ester or ester analogue. This ester/analogue subsequently undergoes spontaneous hydrolysis in water solution in step 5. An unequivocal chemical proof for the intermediate ester formation is provided in Example 5 below.

Scheme I presents the general molecular mechanism for the metal ion dependent peptide bond hydrolysis for the $R_1BXJZR_3R_2$ sequence according to the invention. Wavy lines connecting the main chain with $Y_B$ and $Y_u$ groups denote the remaining atoms of side chains of residues B and J, respectively.

In one aspect of the invention, the said molecular mechanism is realized for $M^{n+}$ denoting $Ni^{2+}$ and for such $R_1BXJZR_3R_2$ sequences, in which B denotes Ser or Thr, and J denotes His. Scheme II illustrates this version of the molecular mechanism according to the invention. Persons skilled in the art will recognize that the mechanism presented in Scheme II corresponds fully to the general mechanism of Scheme I.

Scheme II presents therefore the general molecular mechanism for the metal ion dependent peptide bond hydrolysis for the $R_1BXJZR_3R_2$ sequence according to the invention, in which B represents Ser or Thr, and J represents His.

The molecular mechanism according to the invention requires that residue B in the sequence $R_1BXJZR_3R_2$ contains such group $Y_B$ in its side chain which is capable of accepting an acyl moiety. Therefore, in one embodiment of the invention $Y_B$ is selected from the group comprising hydroxyl, thiol, selenol groups, and B denotes an amino acid residue represented by formula 1, containing such $Y_B$ group. In one preferred embodiment, B represents Ser ($R_{11}$, $R_{12}$ and $R_{13}$ denote hydrogen atoms). In another preferred embodiment, B represents Thr ($R_{11}$ and $R_{12}$ denote hydrogen atoms and $R_{13}$ denotes methyl group).

The molecular mechanism according to the invention also requires residue J in the sequence $R_1BXJZR_3R_2$ to contain such group $Y_J$ in its side chain, which is capable of binding the metal ion $M^{n+}$ in such fashion that $M^{n+}$ can simultaneously coordinate to group $Y_J$ and three peptidic nitrogens of residues J, X, and B. Therefore, in one embodiment of the invention $Y_J$ is selected from the group including, but not limited to inorganic acid moieties, such as sulphate, nitrate or phosphate, organic acid moieties, such as carboxylates, phenols, amines, such as primary, secondary or tertiary aliphatic or alicyclic amines, phosphines, thiols, thioeters, heterocycles, such as derivatives of pyridine, imidazole, triazine, etc. In a particular embodiment residue J denotes Asp, Glu, Tyr, Met, Cys or His. In a preferred embodiment residue J denotes Cys or His. In a more preferred embodiment residue J denotes His.

It has to be noted that the molecular mechanism proposed in the literature for the reaction of hydrolysis of the Ala-Ser and Glu-Ser peptide bonds in $Ni^{2+}$ complexes of $CH_3CO$-Thr-Glu/Ala-Ser-His/Ala-His-Lys-$NH_2$ peptides (Mylonas et al., J. Chem. Soc., Dalton Trans. 2002, 4296-4306) is substantially different from the mechanism according to the present invention, because it assumes (i) the attack of a hydroxide ion (or water molecule) from the bulk of the solution on the peptide bond being hydrolyzed, and (ii) the participation of the Ser side chain in the reaction via the formation of a hydrogen bond with the carbonyl oxygen of the Glu/Ala-Ser peptide bond. It is also wrong, because it explains neither the observed pH dependence of the hydrolysis rate, nor the formation of the intermediate ester with the Ser/Thr hydroxyl group.

It also has to be noted that the molecular mechanism proposed in the literature for the reaction of hydrolysis of the peptide bond preceding Ser/Thr in Ser/Thr-Met/H is sequences in HSA by $Pd^{2+}$ complexes (Zhu and Kostic, Inorg. Chim. Acta 2002, 339, 10'-110), and extended over the reaction of hydrolysis of the Ac-Ser bond in the Ac-Ser-Met complex with $Pt^{2+}$ by Manka et al. (J. Inorg. Biochem. 2004, 98, 1947-1956), is substantially different from that disclosed herein because it occurs in complexes, in which the metal ion forms only three, rather than four bonds at the hydrolyzed sequence. Also the formation of an intermediate ester at the Ser/Thr residue was proposed speculatively there, and was not demonstrated experimentally.

In a further aspect of this invention, it was unexpectedly found that certain specific amino acid substitutions in positions X and Z strongly modulate the maximum rate, as well as the pH profile of the hydrolysis reaction. This aspect was demonstrated by semiquantitative evaluation of progress of hydrolysis in a combinatorial library of peptides substituted in positions X and Z of the test sequence $R_1BXHZR_2$, where B denotes Ser or Thr, $R_1$ denotes $CH_3CO$-Gly-Ala, and $R_2$ denotes Lys-Phe-Leu-$NH_2$ (Example 1 below). The influence of substituents in positions X and Z on the rate of hydrolysis at pH 8.2 was found to be approximately additive. For position X the highest susceptibilities for hydrolysis were found for amino acid residues with highest van der Waals volumes, which measure bulkiness of their side chains. For position Z the highest susceptibilities for hydrolysis were found for amino acid residues with high octanol/water partition coefficients, which measure hydrophobicitiesy of their side chains. Therefore, in a preferred embodiment, the invention relates to the metal ion-dependent hydrolysis of $R_1BXJZR_3R_2$ sequences, wherein a bulky amino acid residue is present in position X and a hydrophobic amino acid residue is present in position Z. X and Z may denote amino acid residues occurring naturally or synthetic. In a further preferred embodiment of this invention B denotes a Ser or a Thr residue, X denotes a H is, Lys, or Arg residue, and J denotes a H is residue. In another preferred embodiment B denotes a Ser residue, X denotes a Lys or Arg residue, and J denotes a His residue. In a preferred embodiment Z denotes a Lys, Val, Arg, Ile, Leu or Trp residue. In a more preferred embodiment Z denotes a Trp residue. In the most preferred embodiment, the invention relates to the metal ion-dependent hydrolysis of $R_1BXJZR_3R_2$ sequences, wherein B denotes a Ser residue, X denotes an Arg residue, J denotes a H is residue and Z denotes a Trp residue.

In another embodiment of the invention, the sequences optimized for hydrolysis can be used to provide functional and specific cleavage sites in recombinant polypeptides, which can be applied to separate C-terminal $R_3R_2$ domains, such as peptides or proteins able to bind specifically to or to 82114020040000360231610149 other interact in other ways with another component or molecule, from N-terminal domains in recombinant polypeptides, wherein these N-terminal domains, represented by $R_1$ in the general sequence $R_1BXJZR_3R_2$, are limited in no way by other components of the recombinant polypeptide, namely B, X, J, Z, $R_2$ or $R_3$, where B represents a residue capable of accepting the $R_1$ acyl group, X represents a bulky residue, J represents a metal ion-binding residue, Z represents a highly hydrophobic residue, and $R_2$ and $R_3$ represent any amino acid sequences.

Examples of $R_2$ functional domains, used widely in the practice of protein purification include hexahistidine peptide, maltose binding protein (MBP), thioredoxin (TRX), glutathione S-transferase (GST) and many others (Terpe, Appl. Microbiol. Biotechnol. 2003, 60, 523-533). In one embodiment of the invention $M^{n+}$ represents any metal ion capable of forming a specific molecular structure with the BXJZ amino acid sequence, present in complexes III and IV in Scheme I, which contains $M^{n+}$ bonded to the group $Y_J$ and peptide nitrogens of residues J, X, and B in a strictly or approximately square-planar geometry. In one embodiment of the invention, $M^{n+}$ is selected from the group containing $Cu^{2+}$, $Cu^{3+}$, $Pt^{2+}$, $Pt^{4+}$, $Pd^{2+}$, $Au^{3+}$, $Ag^{2+}$, $Ni^{2+}$, and $Ni^{3+}$. In a particular embodiment, $M^{n+}$ is selected from the group containing $Cu^{2+}$, $Pt^{2+}$, $Pd^{2+}$, and $Ni^{2+}$. In a preferred embodiment, $M^{n+}$ is selected from the group containing $Cu^{2+}$ and $Ni^{2+}$. In the most preferred embodiment, $M^{n+}$ denotes $Ni^{2+}$.

In a consequence of the reaction mechanism, the rate of hydrolysis is proportional to the concentration of the active complex (III). As a result, the pH profiles of these two quantities match each other closely (FIG. 1). While the optimal pH for this reaction is 10 and higher for most peptides, for optimized sequences, disclosed above, the reaction can proceed effectively at a lower pH, such as 8.2, where the active complex is a minor species among several types of complexes formed simultaneously by $R_1BXJZR_3R_2$ and $M^{n+}$. The formation of the active complex at such lower pH depends on the availability of the metal ion, which is controlled by the overall $M^{n+}$ concentration, as well as by the competition for $M^{n+}$ by other components of reaction mixtures, such as buffers. Therefore, in another embodiment of the invention the hydrolysis of $R_1BXJZR_3R_2$ is performed in such a buffer which does not compete for $M^{n+}$ effectively. Thus, in a preferred embodiment of the present invention the hydrolysis reaction is performed in a buffer weakly coordinating $M^{n+}$ according to the invention, and in the most preferred embodiment the hydrolysis reaction is performed in a buffer which does not coordinate $M^{n+}$. In another preferred embodiment, the buffer is Tris and the metal ion is $Ni^{2+}$. In an even more preferred embodiment, the buffer is Hepes and the metal ion is $Ni^{2+}$.

In one embodiment of the present invention $R_1BXJZR_3R_2$ describes a recombinant polypeptide in which $R_1$ denotes a polypeptide of interest, $R_2$ denotes a functional domain, and $R_3$ denotes empty sequence (is absent from the said sequence). In another embodiment of the invention, the domain $R_2$ is separated from the residue Z by one or more residues, represented by $R_3$, which do not participate in the hydrolysis reaction but separate $R_2$ from the rest of the polypeptide to prevent specific interference with the function of the peptide sequence $R_2$. In a yet another embodiment, the role of $R_3$ is to prevent the inhibition of binding of metal ions according to the invention to the sequence BXJZ.

The present invention poses no limitations on the character of $R_2$ domains. They can be peptides or proteins capable of specific binding to a solid support, reporter domains, targeting sequences, solubilisation domains or domains exerting any other functions.

In a particular embodiment of the invention BXJZ denotes Ser-Arg-His-Trp (SRHW), $R_3$ denotes Ala-Pro (AP) dipeptide sequence, and $R_2$ denotes a hexahistidine (HHHHHH) affinity tag.

In a further embodiment of this invention, the hydrolysis reaction can be performed in a solution, following purification of the recombinant polypeptide on a solid support, such as affinity column. This approach requires a further purification step, to separate the polypeptide of interest $R_1$ from the cleaved off $BXJZR_3R_2$ domain. In another embodiment, the cleavage reaction can be performed while the polypeptide of interest $R_1$ remains attached to the solid support. In this approach, the polypeptide of interest is washed from the solid support together with the hydrolysis buffer, while the cleaved off $BXJZR_3R_2$ domain remains attached to the solid support.

In a preferred embodiment of the present invention, a natural or artificial esterase or a similar catalyst can be added to the reaction mixture to accelerate hydrolysis of ester or ester analogue, which constitutes step 5 of the mechanism presented in Scheme I.

In yet another embodiment of the invention, further reagents can be added to reaction to derivative the C-terminus of $R_1$, thereby accomplishing the synthesis of novel compounds. Such reaction with hydroxylamine, yielding the C-terminal hydroxamate of the target protein, is described in Example 5. Another reaction, with trifluoroethanol, yielding the C-terminal trifluoroethyl ester of the peptide, is described in Example 7.

SHORT DESCRIPTION OF FIGURES

FIG. 1 presents the comparison of pH dependences between the first order rate constant for the hydrolysis of the $CH_3CO$-Gly-Ala-Ser-Arg-His-Trp-Lys-Phe-Leu-$NH_2$ peptide (circles) and the concentration of the active complex III according to Scheme II (solid line).

Figure 2:
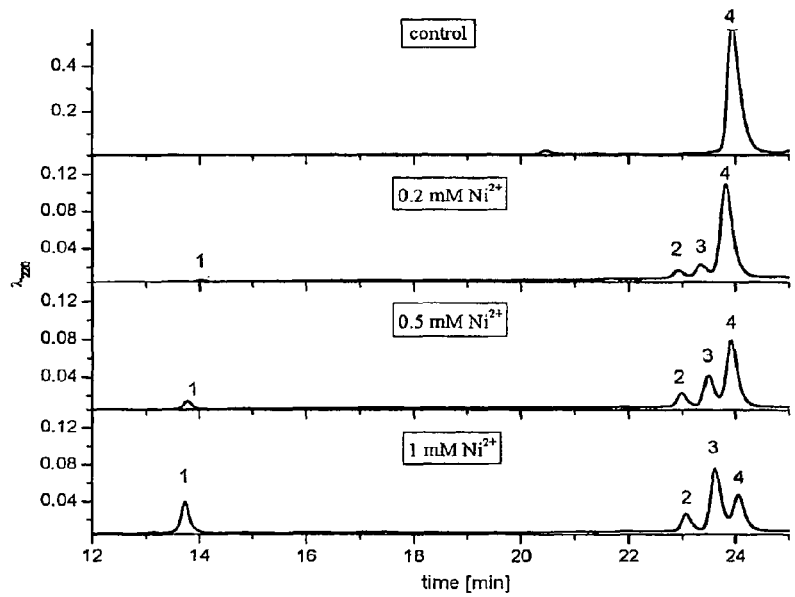

FIG. 2 presents the HPLC chromatogram of products of the reaction of (SPI2)-SRHW-AP-HHHHHH recombinant polypeptide with $Ni^{2+}$ ions under conditions described in Example 6. Labels: 1, SRHW-AP-HHHHHH, molecular mass 1575.73; 2, intermediate product, molecular mass 5866; 3, SPI2 protein, EAAVCTTEWDPVCGKDGKTYSN-LCWLNEAGVGLDHEGEC, theoretical molecular mass 4195.8 (accounting for the formation of two disulfide bridges) measured molecular mass 4309, due to the formation of an adduct with one molecule of trifluoroacetic acid (TFA), HPLC buffer component of molecular mass 114; 4, starting recombinant polypeptide, EAAVCTTEWDPVCGKDGK-TYSNLCWLNEAGVGLDHEGECSRHWAPHHHHHH, theoretical molecular mass 5752.5, measured molecular mass 5866 due to formation of an adduct with one molecule of TFA.

Figure 3:
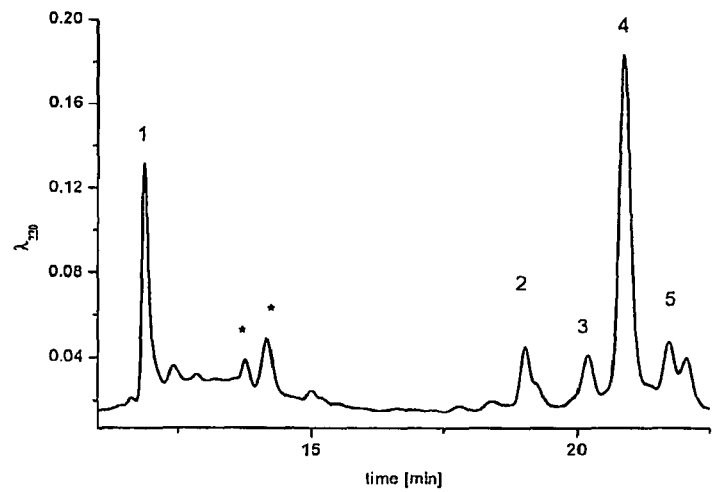

FIG. 3 presents the HPLC chromatogram of products of the reaction of the (SPI2)-SRHW-AP-HHHHHH recombinant polypeptide with $Ni^{2+}$ ions, after incubation with 0.25 M hydroxylamine, as described in Example 7. Labels: *, impurity; 1, SRHW-AP-HHHHHH; 2, intermediate product; 3, hydroxamate of SPI2 protein, molecular mass 4325; 4, starting recombinant polypeptide; 5, SPI2 protein.

Figure 4:
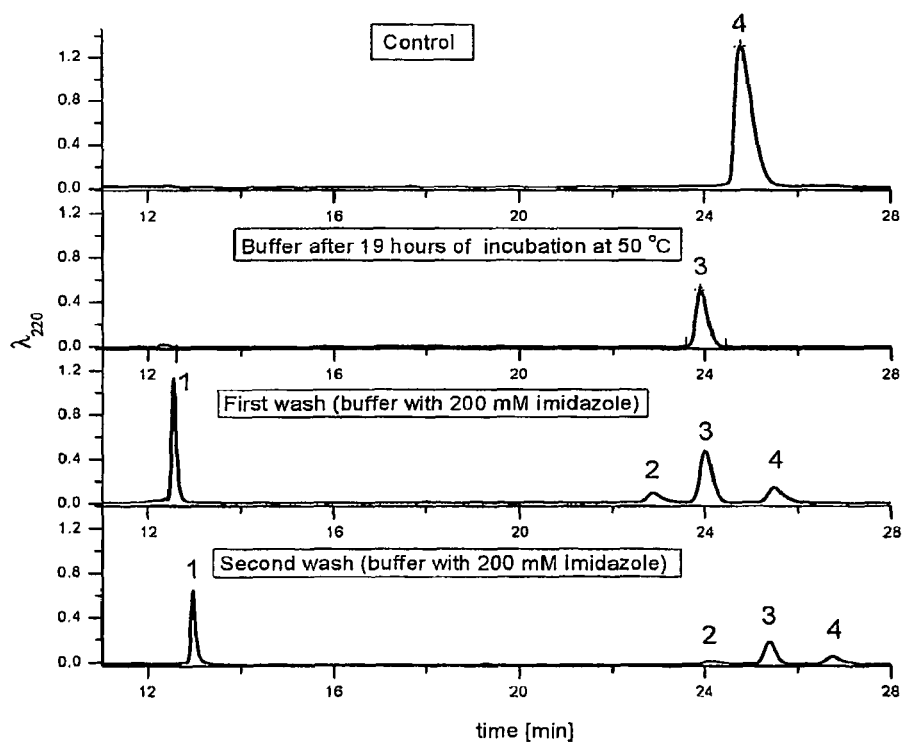

FIG. 4 presents HPLC chromatograms of samples obtained during the cleavage of recombinant polypeptide (SPI2)-SRHW-AP-HHHHHH attached to Ni-NTA agarose in 100 mM Hepes buffer, pH 8.2. Labels 1-4 are identical to those used in FIG. 2.

Figure 5:
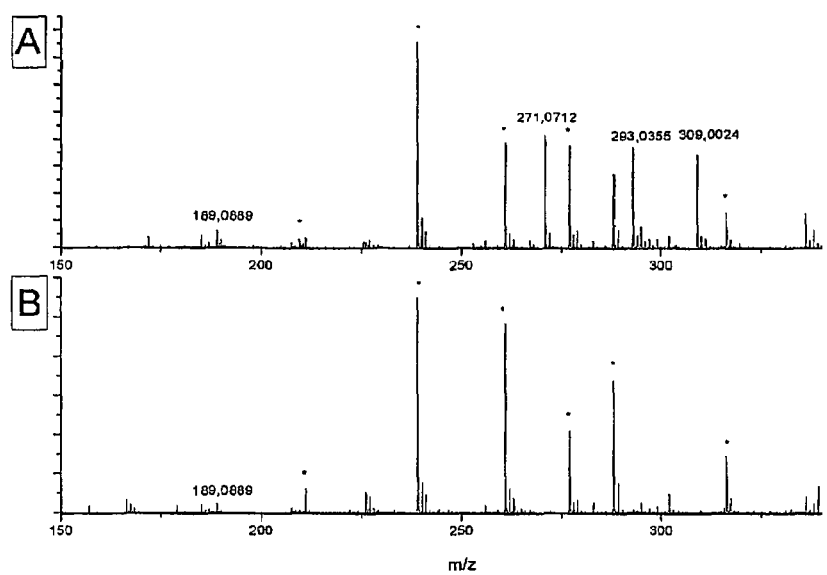

FIG. 5 presents ESI MS spectra, demonstrating the formation of the trifluoroethyl ester of the $CH_3CO$-Gly-Ala peptide, resulting from the $Ni^{2+}$ dependent hydrolysis of the $CH_3CO$-Gly-Ala-Ser-Arg-His-Trp-Lys-Phe-Leu-$NH_2$ peptide. A. The spectrum of the product of the hydrolysis reaction performed in the presence of 50% TFE. B. The spectrum of the product of the hydrolysis reaction performed in the absence of TFE, which was subsequently incubated with 50% TFE. Signal assignments: 189.0889, $CH_3CO$-Gly-Ala+$H^+$; 271.0712, $CH_3CO$-Gly-Ala-$OCH_2CF_3$+$H^+$; 293.0355, $CH_3CO$-Gly-Ala-$OCH_2CF_3$+$Na^+$; 309.0024, $CH_3CO$-Gly-Ala-$OCH_2CF_3$+$K^+$.

Figure 6:
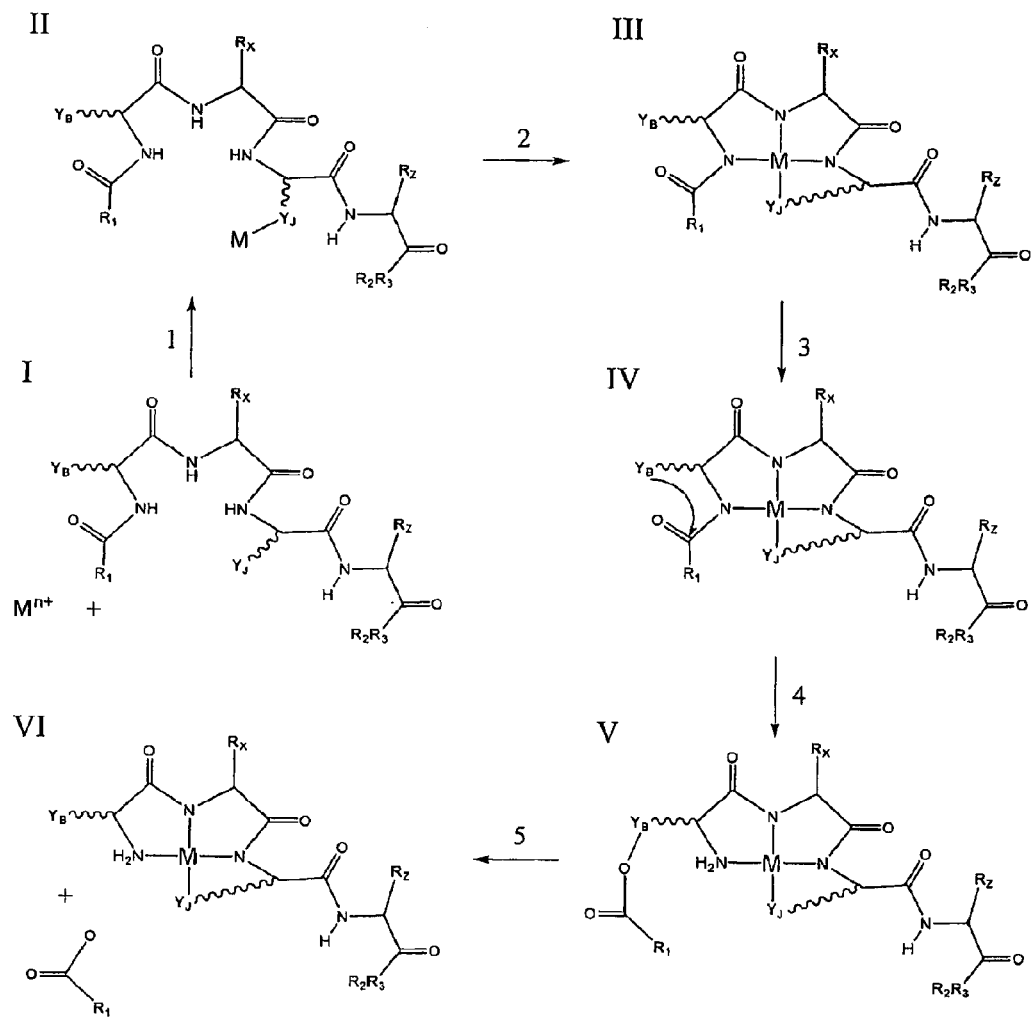

FIG. 6 presents Scheme I showing the general molecular mechanism for the metal ion dependent peptide bond hydrolysis for the $R_1BXJZR_3R_2$ sequence according to the invention. Wavy lines connecting the main chain with $Y_B$ and $Y_u$ groups denote the remaining atoms of side chains of residues B and J, respectively.

Figure 7:
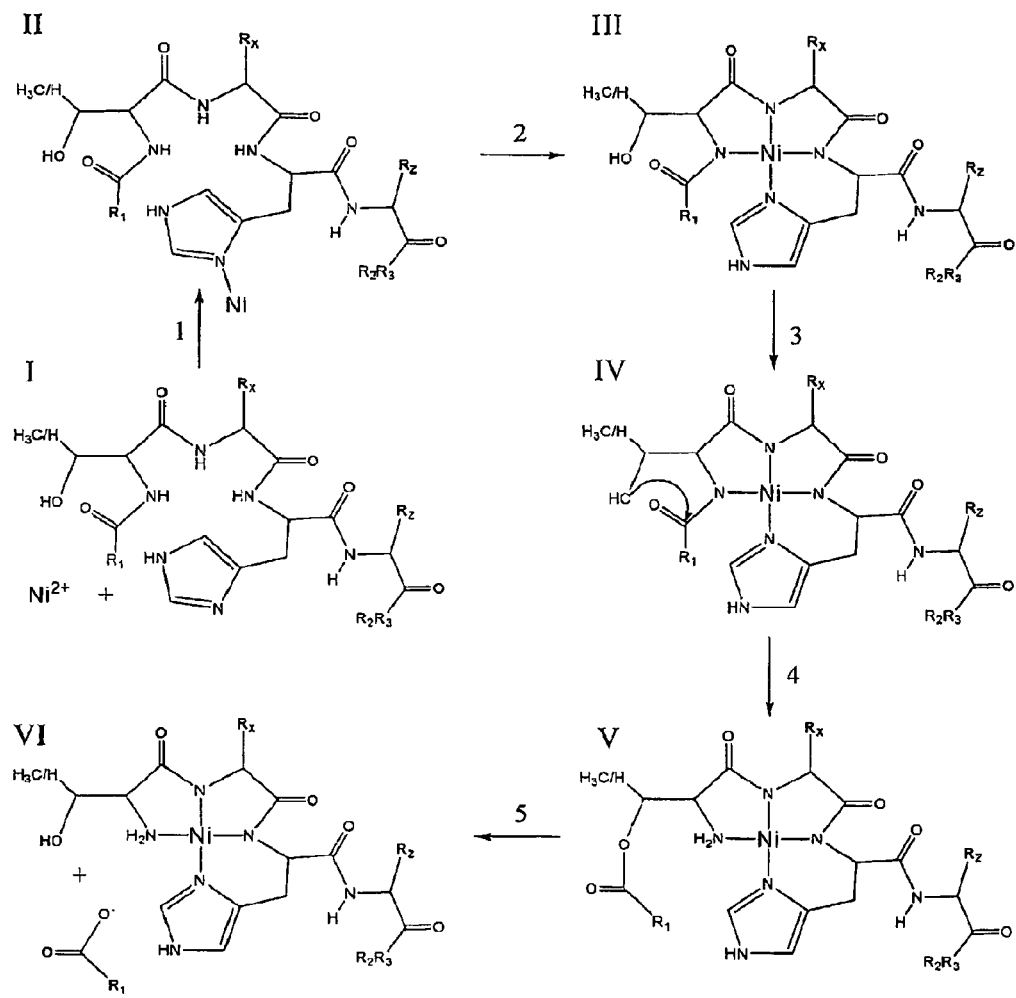

FIG. 7 presents Scheme II showing the general molecular mechanism for the metal ion dependent peptide bond hydrolysis for the $R_1BXJZR_3R_2$ sequence according to the invention, in which B represents Ser or Thr, and J represents His.

The examples of embodiments of the invention are presented below.

Example 1

Optimisation of Positions X and Z in the $R_1BXHZR_2$ Sequence, where B Denotes Ser or Thr, for the Acceleration of $Ni^{2+}$ Dependent Hydrolysis, Using Combinatorial Synthesis and Mass Spectrometry The sequence $CH_3CO$-Gly-Ala-Ser/Thr-X-His-Z-Lys-Phe-Leu-$NH_2$ was designed so that the fixed $R_1$ and $R_2$ sequences, $CH_3CO$-Gly-Ala, and Lys-Phe-Leu-$NH_2$, respectively, allowed optimal detection by MALDI-TOF mass spectrometry of substrates as well as expected products, Ser/Thr-X-His-Z-Lys-Phe-Leu-$NH_2$ and assured separation between the clusters of signals for substrates and products in sublibraries (see below).

Residues in position X included all amino acids commonly present in proteins, except for Asp, Glu, and Cys. The former two contain carboxylates in their side chains, which may bind $Ni^{2+}$ in a way which would quench or slow down the hydrolysis reaction. The Cys residue may do the same, and also may engage in side reactions with $Ni^{2+}$ ions, including redox processes (for example see Bal and Kasprzak, Toxicol. Lett. 2002, 127, 55-62). Only the Cys residue was eliminated from position Z, for the same reasons.

The synthesis of the library was accomplished on a RINK amide resin (Novabiochem) on a 800 mg scale, according to a typical Fmoc protocol (Fields, Meth. Enzymol. Vol. 289). The resin-attached Leu-Phe-Lys peptide was synthesised first and coupled with the isokinetic mixture of 19 amino acids selected for position Z, and then with the His residue. The resin carrying the library of pentapeptides was divided into Ser and Thr halves at this stage, and each of these halves into 17 portions, which were coupled with individual amino acids selected for position X. The coupling with Ser or Thr as appropriate, additions of Ala and Gly residues, acetylation of Gly, deprotection and cleavage from the resin were accomplished subsequently. Each of the resulting 34 samples of sublibraries randomized at position X was separated into two portions, one for the reaction at 37° C. and another for the reaction at 45° C. The hydrolysis reactions were accomplished in 10 mM Tris buffers at pH 8.2. The total concentrations of peptide mixtures and $Ni^{2+}$ ions were 1 mM and 2 mM, respectively. The pH for the reaction was chosen as selective for highly reactive sequences.

The detection of reaction products was accomplished with the use of a MALDI-TOF mass spectrometer (Micromass). The aliquots were removed from reaction mixtures and measured by MS at 2, 4, 6, and 8 hours of incubation. The progress of reaction was evaluated by visual detection in mass spectra of appearance of signals corresponding to expected products of hydrolysis, Ser/Thr-X-His-Z-Lys-Phe-Leu-$NH_2$, at given measurement times, $t_m$. The formula used for semiquantitative evaluation of reaction progress had a following form: score=$24/t_m$, therefore a given peptide was assigned a score of 12, if it was seen to be partially hydrolysed at 2 hours, a score of 6 for detection at 4 hours, a score of 4 for detection at 6 hours, a score of 3 for detection at 8 hours, and a score of 0 if no trace of the product of hydrolysis was seen after 8 hours of incubation. For the most active peptides, for which the formation of Ser/Thr-X-His-Z-Lys-Phe-Leu-$NH_2$ products was seen at 2 hours, the progress of reaction was additionally controlled at longer incubation times. Also the decrease of signals of substrates was controlled in these cases.

Residues X and Z were then sorted according to various molecular parameters, describing their physical properties (Carugo, In Silico Biol. 2003, 3, 0035). Van der Waals volumes, which correspond to the bulkiness of their side chains and octanol/water partition coefficients, which correspond to hydrophobicities of their side chains were found to provide the best positive correlations to observed scores for positions X and Z, respectively. The results for individual peptides, ordered according to these parameters, are presented in Table 1A-D. The contributions of substituents X and Z to the scores for hydrolysis were found to be approximately additive, with some positive or (more often) negative deviations, indicative of the presence of secondary specific interactions between the residues. The Ser library provided a higher number of reactive peptides than the Thr library. Following the additivity of effects, the scores were also summed up in lines and columns of Table 1A-D, thereby creating final rankings for preferred substitutions in positions X and Z.

TABLE 1

| | Z | | | | | | | | | | | | | | | | | |
|---|---|---|---|---|---|---|---|---|---|---|---|---|---|---|---|---|---|---|
| X | E | D | N | Q | S | A | P | H | T | G | V | Y | M | I | L | K | F | W | R | Sc. |

A. The hydrolysis scores from MALDI-TOF screening of the library of peptides $CH_3CO$-Gly-Ala-Ser-X-His-Z-Lys-Phe-Leu-$NH_2$, incubated with $Ni^{2+}$ at 45° C.

| X | E | D | N | Q | S | A | P | H | T | G | V | Y | M | I | L | K | F | W | R | Sc. |
|---|---|---|---|---|---|---|---|---|---|---|---|---|---|---|---|---|---|---|---|---|
| G | 0 | 0 | 0 | 0 | 0 | 0 | 0 | 0 | 0 | 0 | 3 | 0 | 0 | 3 | 3 | 3 | 0 | 4 | 3 | 19 |
| A | 0 | 0 | 0 | 0 | 0 | 3 | 0 | 4 | 0 | 0 | 3 | 3 | 0 | 4 | 4 | 6 | 3 | 6 | 6 | 42 |
| S | 3 | 3 | 0 | 0 | 3 | 3 | 0 | 3 | 0 | 3 | 4 | 3 | 3 | 6 | 6 | 6 | 3 | 12 | 6 | 67 |
| P | 0 | 0 | 0 | 0 | 0 | 0 | 0 | 0 | 0 | 0 | 0 | 0 | 0 | 0 | 0 | 0 | 0 | 0 | 0 | 0 |
| T | 0 | 0 | 0 | 0 | 0 | 0 | 0 | 3 | 0 | 0 | 6 | 3 | 0 | 6 | 6 | 6 | 3 | 6 | 6 | 45 |
| N | 0 | 0 | 0 | 0 | 0 | 0 | 0 | 3 | 0 | 0 | 3 | 3 | 0 | 4 | 4 | 4 | 3 | 6 | 6 | 36 |
| V | 0 | 0 | 0 | 0 | 0 | 0 | 0 | 3 | 0 | 0 | 3 | 3 | 0 | 3 | 3 | 4 | 3 | 4 | 3 | 29 |
| Q | 0 | 0 | 0 | 0 | 0 | 3 | 0 | 0 | 0 | 0 | 4 | 4 | 3 | 6 | 6 | 6 | 4 | 6 | 6 | 48 |
| L | 0 | 0 | 0 | 0 | 0 | 0 | 0 | 0 | 0 | 0 | 3 | 3 | 0 | 0 | 0 | 4 | 3 | 4 | 4 | 21 |
| I | 0 | 0 | 0 | 0 | 0 | 0 | 0 | 3 | 0 | 0 | 3 | 0 | 0 | 3 | 3 | 4 | 0 | 3 | 3 | 22 |
| H | 0 | 0 | 0 | 0 | 0 | 0 | 0 | 0 | 0 | 0 | 6 | 4 | 0 | 6 | 6 | 12 | 3 | 12 | 6 | 55 |
| M | 0 | 0 | 0 | 0 | 3 | 3 | 0 | 3 | 0 | 0 | 6 | 4 | 3 | 12 | 12 | 6 | 4 | 6 | 6 | 68 |
| K | 3 | 0 | 0 | 0 | 0 | 0 | 0 | 3 | 0 | 0 | 6 | 4 | 4 | 12 | 12 | 12 | 4 | 12 | 6 | 78 |
| F | 3 | 0 | 0 | 0 | 0 | 3 | 0 | 6 | 0 | 0 | 6 | 6 | 3 | 6 | 6 | 6 | 6 | 6 | 6 | 63 |
| Y | 0 | 0 | 0 | 0 | 0 | 0 | 0 | 4 | 0 | 0 | 4 | 4 | 0 | 6 | 6 | 6 | 4 | 6 | 6 | 46 |

TABLE 1-continued

| | | | | | | | | Z | | | | | | | | | | | |
|---|---|---|---|---|---|---|---|---|---|---|---|---|---|---|---|---|---|---|---|
| X | E | D | N | Q | S | A | P | H | T | G | V | Y | M | I | L | K | F | W | R | Sc. |
| R | 3 | 0 | 0 | 0 | 4 | 6 | 0 | 4 | 3 | 6 | 12 | 6 | 3 | 12 | 12 | 12 | 4 | 12 | 12 | 111 |
| W | 0 | 0 | 0 | 0 | 0 | 3 | 0 | 3 | 0 | 3 | 12 | 6 | 3 | 12 | 12 | 12 | 4 | 6 | 6 | 82 |
| Sc. | 12 | 3 | 0 | 0 | 10 | 24 | 0 | 42 | 3 | 12 | 84 | 56 | 22 | 101 | 101 | 109 | 51 | 111 | 91 | 832 |

B. The hydrolysis scores from MALDI-TOF screening of the library of peptides CH$_3$CO-Gly-Ala-Ser-X-His-Z-Lys-Phe-Leu-NH$_2$, incubated with Ni$^{2+}$ at 37° C.

| X | E | D | N | Q | S | A | P | H | T | G | V | Y | M | I | L | K | F | W | R | Sc. |
|---|---|---|---|---|---|---|---|---|---|---|---|---|---|---|---|---|---|---|---|---|
| G | 0 | 0 | 0 | 0 | 0 | 0 | 0 | 0 | 0 | 0 | 0 | 0 | 0 | 0 | 0 | 0 | 0 | 3 | 3 | 6 |
| A | 0 | 0 | 0 | 0 | 0 | 0 | 0 | 0 | 0 | 0 | 0 | 0 | 0 | 0 | 0 | 3 | 0 | 4 | 3 | 10 |
| S | 0 | 0 | 0 | 0 | 0 | 0 | 0 | 0 | 0 | 0 | 3 | 3 | 3 | 6 | 6 | 4 | 3 | 6 | 6 | 40 |
| P | 0 | 0 | 0 | 0 | 0 | 0 | 0 | 0 | 0 | 0 | 0 | 0 | 0 | 0 | 0 | 0 | 0 | 0 | 0 | 0 |
| T | 0 | 0 | 0 | 0 | 0 | 0 | 0 | 0 | 0 | 0 | 0 | 0 | 0 | 4 | 4 | 3 | 0 | 4 | 3 | 18 |
| N | 0 | 0 | 0 | 0 | 0 | 0 | 0 | 0 | 0 | 0 | 3 | 3 | 0 | 4 | 4 | 4 | 3 | 6 | 6 | 33 |
| V | 0 | 0 | 0 | 0 | 0 | 0 | 0 | 3 | 0 | 0 | 0 | 0 | 0 | 3 | 3 | 3 | 0 | 4 | 3 | 19 |
| Q | 0 | 0 | 0 | 0 | 0 | 0 | 0 | 0 | 0 | 0 | 0 | 3 | 0 | 6 | 6 | 4 | 3 | 6 | 6 | 34 |
| L | 0 | 0 | 0 | 0 | 0 | 0 | 0 | 0 | 0 | 0 | 0 | 0 | 0 | 3 | 3 | 3 | 0 | 3 | 3 | 15 |
| I | 0 | 0 | 0 | 0 | 0 | 0 | 0 | 3 | 0 | 0 | 3 | 0 | 0 | 3 | 3 | 3 | 0 | 3 | 3 | 21 |
| H | 0 | 0 | 0 | 0 | 0 | 3 | 0 | 0 | 0 | 3 | 6 | 3 | 0 | 6 | 6 | 6 | 3 | 6 | 4 | 46 |
| M | 0 | 0 | 0 | 0 | 0 | 0 | 0 | 0 | 0 | 0 | 3 | 3 | 3 | 4 | 4 | 3 | 3 | 4 | 4 | 31 |
| K | 0 | 0 | 0 | 0 | 0 | 0 | 0 | 4 | 0 | 0 | 4 | 4 | 3 | 6 | 6 | 6 | 4 | 12 | 4 | 53 |
| F | 0 | 0 | 0 | 0 | 0 | 0 | 0 | 3 | 0 | 0 | 3 | 3 | 0 | 4 | 4 | 4 | 3 | 4 | 4 | 32 |
| Y | 0 | 0 | 0 | 0 | 0 | 0 | 0 | 4 | 0 | 0 | 6 | 3 | 0 | 4 | 4 | 4 | 3 | 6 | 4 | 38 |
| R | 0 | 0 | 0 | 0 | 3 | 3 | 0 | 4 | 0 | 3 | 6 | 4 | 3 | 12 | 12 | 6 | 4 | 12 | 4 | 76 |
| W | 0 | 0 | 0 | 0 | 0 | 0 | 0 | 4 | 0 | 0 | 3 | 0 | 0 | 6 | 6 | 4 | 3 | 4 | 3 | 33 |
| Sc. | 0 | 0 | 0 | 0 | 3 | 6 | 0 | 25 | 0 | 6 | 40 | 29 | 12 | 71 | 71 | 60 | 32 | 87 | 63 | 505 |

C. The hydrolysis scores from MALDI-TOF screening of the library of peptides CH$_3$CO-Gly-Ala-Thr-X-His-Z-Lys-Phe-Leu-NH$_2$, incubated with Ni$^{2+}$ at 45° C.

| X | E | D | N | Q | S | A | P | H | T | G | V | Y | M | I | L | K | F | W | R | Sc. |
|---|---|---|---|---|---|---|---|---|---|---|---|---|---|---|---|---|---|---|---|---|
| G | 0 | 0 | 0 | 0 | 0 | 0 | 0 | 0 | 0 | 0 | 0 | 0 | 0 | 0 | 0 | 0 | 0 | 0 | 0 | 0 |
| A | 0 | 0 | 0 | 0 | 0 | 0 | 0 | 0 | 0 | 0 | 0 | 0 | 0 | 0 | 0 | 0 | 0 | 0 | 0 | 0 |
| S | 0 | 0 | 0 | 0 | 0 | 0 | 0 | 0 | 0 | 0 | 0 | 0 | 0 | 0 | 0 | 0 | 0 | 0 | 0 | 0 |
| P | 0 | 0 | 0 | 0 | 0 | 0 | 0 | 0 | 0 | 0 | 0 | 0 | 0 | 0 | 0 | 0 | 0 | 0 | 0 | 0 |
| T | 0 | 0 | 0 | 0 | 0 | 0 | 0 | 0 | 0 | 0 | 0 | 0 | 0 | 0 | 0 | 0 | 0 | 0 | 3 | 3 |
| N | 0 | 0 | 0 | 0 | 0 | 0 | 0 | 0 | 0 | 0 | 0 | 0 | 0 | 0 | 0 | 0 | 0 | 3 | 3 | 6 |
| V | 0 | 0 | 0 | 0 | 0 | 0 | 0 | 0 | 0 | 0 | 0 | 0 | 0 | 0 | 0 | 0 | 0 | 3 | 3 | 6 |
| Q | 0 | 0 | 0 | 0 | 0 | 0 | 0 | 0 | 0 | 0 | 0 | 0 | 0 | 3 | 3 | 3 | 0 | 4 | 4 | 17 |
| L | 0 | 0 | 0 | 0 | 0 | 0 | 0 | 0 | 0 | 0 | 0 | 0 | 0 | 0 | 0 | 3 | 0 | 3 | 3 | 9 |
| I | 0 | 0 | 0 | 0 | 0 | 0 | 0 | 0 | 0 | 0 | 0 | 0 | 0 | 0 | 0 | 3 | 0 | 3 | 3 | 9 |
| H | 0 | 0 | 0 | 0 | 4 | 4 | 0 | 4 | 4 | 4 | 6 | 6 | 4 | 12 | 12 | 12 | 6 | 12 | 6 | 96 |
| M | 0 | 0 | 0 | 0 | 0 | 0 | 0 | 0 | 0 | 0 | 0 | 0 | 0 | 0 | 0 | 3 | 0 | 3 | 4 | 10 |
| K | 0 | 0 | 0 | 0 | 0 | 3 | 0 | 4 | 0 | 0 | 6 | 6 | 4 | 12 | 12 | 12 | 6 | 12 | 12 | 89 |
| F | 0 | 0 | 0 | 0 | 0 | 0 | 0 | 0 | 0 | 0 | 0 | 0 | 0 | 0 | 0 | 3 | 0 | 3 | 4 | 10 |
| Y | 0 | 0 | 0 | 0 | 0 | 0 | 0 | 0 | 0 | 0 | 0 | 0 | 0 | 0 | 0 | 4 | 0 | 4 | 4 | 12 |
| R | 0 | 0 | 0 | 0 | 0 | 3 | 0 | 4 | 0 | 0 | 4 | 6 | 4 | 12 | 12 | 12 | 4 | 12 | 6 | 79 |
| W | 0 | 0 | 0 | 0 | 0 | 0 | 0 | 0 | 0 | 0 | 0 | 3 | 3 | 3 | 3 | 4 | 0 | 4 | 4 | 21 |
| Sc. | 0 | 0 | 0 | 0 | 4 | 10 | 0 | 12 | 4 | 4 | 16 | 18 | 15 | 42 | 42 | 59 | 16 | 66 | 59 | 367 |

D. The hydrolysis scores from MALDI-TOF screening of the library of peptides CH$_3$CO-Gly-Ala-Thr-X-His-Z-Lys-Phe-Leu-NH$_2$, incubated with Ni$^{2+}$ at 37° C.

| X | E | D | N | Q | S | A | P | H | T | G | V | Y | M | I | L | K | F | W | R | Sc. |
|---|---|---|---|---|---|---|---|---|---|---|---|---|---|---|---|---|---|---|---|---|
| G | 0 | 0 | 0 | 0 | 0 | 0 | 0 | 0 | 0 | 0 | 0 | 0 | 0 | 0 | 0 | 0 | 0 | 0 | 0 | 0 |
| A | 0 | 0 | 0 | 0 | 0 | 0 | 0 | 0 | 0 | 0 | 0 | 0 | 0 | 0 | 0 | 0 | 0 | 0 | 0 | 0 |
| S | 0 | 0 | 0 | 0 | 0 | 0 | 0 | 0 | 0 | 0 | 0 | 0 | 0 | 0 | 0 | 0 | 0 | 0 | 0 | 0 |
| V | 0 | 0 | 0 | 0 | 0 | 0 | 0 | 0 | 0 | 0 | 0 | 0 | 0 | 0 | 0 | 0 | 0 | 0 | 0 | 0 |
| T | 0 | 0 | 0 | 0 | 0 | 0 | 0 | 0 | 0 | 0 | 0 | 0 | 0 | 0 | 0 | 0 | 0 | 0 | 0 | 0 |
| N | 0 | 0 | 0 | 0 | 0 | 0 | 0 | 0 | 0 | 0 | 0 | 0 | 0 | 0 | 0 | 0 | 0 | 0 | 0 | 0 |
| V | 0 | 0 | 0 | 0 | 0 | 0 | 0 | 0 | 0 | 0 | 0 | 0 | 0 | 0 | 0 | 0 | 0 | 0 | 0 | 0 |
| Q | 0 | 0 | 0 | 0 | 0 | 0 | 0 | 0 | 0 | 0 | 0 | 0 | 0 | 0 | 0 | 0 | 0 | 3 | 3 | 6 |
| L | 0 | 0 | 0 | 0 | 0 | 0 | 0 | 0 | 0 | 0 | 0 | 0 | 0 | 0 | 0 | 0 | 0 | 3 | 0 | 3 |
| I | 0 | 0 | 0 | 0 | 0 | 0 | 0 | 0 | 0 | 0 | 0 | 0 | 0 | 0 | 0 | 0 | 0 | 3 | 0 | 3 |
| H | 0 | 0 | 0 | 0 | 0 | 0 | 0 | 3 | 0 | 0 | 0 | 0 | 0 | 3 | 3 | 6 | 0 | 12 | 6 | 33 |
| M | 0 | 0 | 0 | 0 | 0 | 0 | 0 | 0 | 0 | 0 | 0 | 0 | 0 | 0 | 0 | 0 | 0 | 3 | 3 | 6 |
| K | 0 | 0 | 0 | 0 | 0 | 0 | 0 | 0 | 0 | 0 | 3 | 3 | 3 | 4 | 4 | 3 | 3 | 6 | 4 | 33 |
| F | 0 | 0 | 0 | 0 | 0 | 0 | 0 | 0 | 0 | 0 | 0 | 0 | 0 | 0 | 0 | 3 | 0 | 0 | 3 | 6 |
| Y | 0 | 0 | 0 | 0 | 0 | 0 | 0 | 0 | 0 | 0 | 0 | 0 | 0 | 0 | 0 | 3 | 0 | 3 | 4 | 10 |
| R | 0 | 0 | 0 | 0 | 0 | 0 | 0 | 0 | 0 | 0 | 3 | 0 | 0 | 3 | 4 | 3 | 6 | 6 | 6 | 3 | 12 | 4 | 50 |
| W | 0 | 0 | 0 | 0 | 0 | 0 | 0 | 0 | 0 | 0 | 0 | 0 | 0 | 0 | 0 | 0 | 0 | 4 | 3 | 3 | 10 |
| Sc. | 0 | 0 | 0 | 0 | 0 | 0 | 0 | 6 | 0 | 0 | 6 | 7 | 6 | 13 | 13 | 25 | 6 | 48 | 30 | 160 |

Example 2

Quantitative Kinetic Studies of CH₃CO-Gly-Ala-B-X-His-Z-Phe-Leu-NH₂ Peptides, Selected in Combinatorial Library Screening The title octapeptides were synthesised according to a typical Fmoc protocol (Fields, Meth. Enzymol. Vol. 289). The list of variable BXHZ sequences is given in Table 2, along with 1$^{st}$ order rate constants determined at 45° C., pH 8.2 (20 mM Tris buffer) for 1 mM peptide and Ni$^{2+}$ concentrations. The rate constants were obtained by separating and quantifying the substrates and products at various incubation times using HPLC, followed by the fitting of the 1st order rate function to these data. The substrate and product peaks were identified by MALDI-TOF MS.

TABLE 2

1$^{st}$ order rate constants for the hydrolysis of 1 mM CH₃CO-Gly-Ala-B-X-His-Z-Phe-Leu-NH₂ peptides selected on the basis of Example 1 in the presence of 1 mM Ni$^{2+}$ at 45° C. and pH 8.2 (20 mM Tris).

| -BXHZ- sequence | k ± S.D. (s$^{-1}$ · 10$^{-5}$) |
|---|---|
| -SRHW- | 28.8 ± 0.8 |
| -THHW- | 13.7 ± 0.5 |
| -SKHW- | 11 ± 1 |
| -TRHW- | 10.2 ± 0.7 |
| -TKHW- | 9.1 ± 0.6 |
| -SRHK- | 4.0 ± 0.2 |
| -SWHL- | 3.7 ± 0.4 |
| -SWHI- | 3 ± 1 |
| -THHK- | 1.01 ± 0.09 |

The above results indicate that all peptides selected by combinatorial screening were hydrolysed at pH 8.2, but the hydrolysis rate constants at 45° C. varied by a factor of 30 over the group studied. The sequence -Ser-Arg-His-Trp- (-SRHW-) was found to be the most active among those selected, and was thus used in further studies.

Example 3

Dependence of the Rate of Hydrolysis of the Ala-Ser Peptide Bond in the CH₃CO-Gly-Ala-Ser-Arg-His-Trp-Lys-Phe-Leu-NH₂ Peptide on pH, Buffer, and Ni$^{2+}$ Excess The title peptide was synthesised according to a standard Fmoc protocol (Fields, Meth. Enzymol. Vol. 289). The pH dependence of the formation of the active complex of the title peptide, represented by the structure (III) in Scheme 2, was determined by potentiometry at 25° C., as described in Krezel et al., Chem. Res. Toxicol. 2003, 16, 855-864. The rate of peptide hydrolysis was studied by HPLC (as in Example 2) in a series of mixed phosphate/Tris/Borax buffers (40/20/20 mM) at 25° C. and pH between 6 and 12.5, with peptide and Ni$^{2+}$ concentrations equal to 1 mM. As presented in FIG. 1, the rate of hydrolysis matched the formation of the active complex quantitatively.

The dependence of the rate of hydrolysis on the buffer used was studied at 25° C. separately in 20 mM Tris, Hepes and sodium phosphate buffers, all at pH 8.2, for 1 mM peptide and 1.2 mM Ni$^{2+}$. The results are presented in Table 3.

TABLE 3

The dependence of the 1$^{st}$ order rate constant for the hydrolysis of the title peptide on the buffer used (20 mM) at 25° C. and pH 8.2, for 1 mM peptide and 1.2 mM Ni$^{2+}$.

| buffer | κ ± S.D. (s$^{-1}$ × 10$^{-5}$) |
|---|---|
| Tris | 4.8 ± 0.5 |
| Hepes | 5.9 ± 0.8 |
| phosphate | 0.74 ± 0.09 |

It was clearly demonstrated that Hepes is the optimal buffer for Ni$^{2+}$-dependent hydrolysis at pH 8.2, Tris is slightly inferior, while phosphate is inappropriate. The extent of inhibition of peptide hydrolysis is correlated to relative abilities of these buffers to compete for Ni$^{2+}$ with the title peptide at pH 8.2: Hepes does not bind Ni$^{2+}$, Tris binds weakly, while phosphate is a relatively strong competitor (see Krezel et al., Chem. Res. Toxicol. 2003, 16, 855-864). This order is highly probable to be maintained for other M$^{n+}$ according to the invention (see Sokolowska and Bal, J. Inorg. Biochem. 2005, 99, 1653-1660).

The dependence of the rate of hydrolysis of the title peptide on the molar ratio of Ni$^{2+}$ to peptide was studied at 25° C. and pH 8.2, for 1 mM peptide. The reaction rate constant k was 4.3±0.2 s$^{-1}$×10$^{-5}$ for the Ni$^{2+}$ to peptide molar ratio of 1.2 and 4.72±0.01 s$^{-1}$×10$^{-5}$ for the Ni$^{2+}$ to peptide molar ratio of 5. This experiment demonstrated that the hydrolysis of the title peptide was somewhat faster for a severalfold molar excess of Ni$^{2+}$, compared to the equimolar system.

The results presented in this Example demonstrate that the rate of hydrolysis according to the invention depends primarily on the concentration of the active complex, which can be maximized by assuring an excess of M$^{n+}$ over the peptide being hydrolyzed, by avoiding M$^{n+}$ competitors in reaction mixtures, and by adjusting the pH of reaction.

A person skilled in the art will understand that all properties of the hydrolysis reaction established for model peptides and disclosed above will apply to the process of hydrolysis of fusion protein recombinant polypeptide according to the invention.

Example 4

Ni$^{2+}$-Dependent Release of SPI2 Protein from its Fusion in Solution

The suitability of the reaction according to the invention for the cleavage of a functional domain from a polypeptide of interest was tested on a (SPI2)-SRHW-AP-HHHHHH recombinant polypeptide. SPI2 is a single domain Kazal type proteinase inhibitor. The biologically active recombinant SPI2, extended C-terminally with the myc epitope, followed by the HHHHHH sequence (hexahistidine peptide) was previously expressed in a *Pichia pastoris* system (Grzelak et al., WO2005007693). The (SPI2)-SRHW-AP-HHHHHH recombinant polypeptide was cloned under the control of the AOX promoter in the pPICZaB vector (Invitrogen), and then expressed and purified by affinity chromatography on Ni-NTA-agarose and by HPLC, as described for an analogous protein containing the myc epitope (Grzelak et al., WO2005007693).

The initial experiment was carried out in 1 M Hepes buffer at pH 8.2 and 45° C., for the recombinant polypeptide at a concentration of 16 μM and Ni$^{2+}$ concentrations of 0.2, 0.5 and 1 mM. After 16 hours of incubation the samples were analyzed by HPLC (C18 column from ACE, 250×4.6 mm, 20-25% acetonitrile/0.1% TFA gradient over 25 min. at 1 ml/min). The results are presented in FIG. 2. The molecular masses of collected HPLC peaks, measured using ESI MS (Q-Tof1, Micromass), confirmed cleavage of the SRHW-AP-HHHHHH domain without side products. As seen in FIG. 2, differently to peptide studies, substantial amounts of an intermediate hydrolysis product, with the mass identical to the starting recombinant polypeptide, were observed.

Example 5

The Formation of a C-Terminal Hydroxamate of SPI2 Resulting from the Addition of Hydroxylamine to the Intermediate Product of the $Ni^{2+}$-Dependent Release of SPI2 Protein from its Fusion in Solution The experiment with hydroxylamine provided direct evidence for the presence of an ester moiety in the intermediate product. Hydroxylamine is known to react specifically with esters and form hydroxamic acids (Jencks et al., J. Biol. Chem. 1960, 235, 3608-3614). The recombinant polypeptide from Example 4 was incubated in 1 M Hepes buffer, pH 8.2 with 5 mM $Ni^{2+}$ at 37° C. for 6 hours. Hydroxylamine was then added to the final concentration of 0.25 M, and pH was set to 6.0. The reaction mixture was subsequently incubated for 48 hours at 37° C., and then analyzed by HPLC under conditions given in Example 4. FIG. 3 presents the resulting chromatogram. Molecular masses of collected peaks were measured with ESI MS. The formation of SPI2 hydroxamate was confirmed by the detection of a SPI2 analogue with the mass increased by 16 Da (4325 vs. 4309) upon the hydroxylamine treatment.

Example 6

$Ni^{2+}$-Dependent Release of SPI2 Protein from the Recombinant Polypeptide Attached to a Solid Support The recombinant polypeptide from Example 4 (100 µl of a 140 µM solution) was loaded on 200 µl of Ni-NTA-agarose (Invitrogen), according to the manufacturer's instruction, and incubated in 100 mM Hepes buffer, pH 8.2 with 5 mM $Ni^{2+}$ at 50° C. without shaking. The incubation buffer (500 µl) was removed after 19 hours. Then the unreacted polypeptide and the cleaved off SRHW-AP-HHHHHH domain were washed from the column with two 400 µl portions of 200 mM imidazole, pH 7.4. The samples were analyzed by HPLC under conditions given in Example 4. FIG. 4 presented chromatograms of the control recombinant polypeptide, incubation buffer and both wash fractions. Masses of polypeptides were measured by ESI-MS. The yield of purified SPI2 was 88%. SPI2 obtained from this procedure was fully active, as determined according to Chavira et al., Anal. Biochem. 1984, 136, 446-450.

Example 7

Modification of the C-Terminus of $CH_3CO$-Gly-Ala Dipeptide During the Reaction of Hydrolysis of $CH_3CO$-GASRHWKFL-$NH_2$ Peptide in the Presence of $Ni^{2+}$ Ions and 50% Trifluoroethanol in Solution The experiment with trifluoroethanol (TFE) confirmed the possibility of modifying the C-terminus of a polypeptide of interest in a reaction of the intermediate product with another compound. The title peptide was incubated in 10 mM Hepes buffer, pH 8.2 with 5 mM $Ni^{2+}$ in the presence of 50% trifluoroethanol at 50° C. for 4 hours. The reaction mixture was subsequently analyzed by ESI MS. The formation of an ester of the $CH_3CO$-Gly-Ala dipeptide with trifluoroethanol was confirmed by detecting the reaction product with the mass increased by 82 Da relative to the mass of $CH_3CO$-Gly-Ala (189 versus 271) (FIG. 5B). As a control, the complete reaction of hydrolysis of the $CH_3CO$-GASRHWKFL-$NH_2$ peptide was performed (20 hours at 50° C.), followed by the addition of 50% TFE, incubation under the same conditions for 4 hours, and analysis of the reaction mixture using ESI MS. The mass of 271 was not detected, but a signal for the mass of 189 was found (FIG. 5A), which means that under these conditions the ester of $CH_3CO$-Gly-Ala dipeptide with trifluoroethanol was formed only by solvolysis of the intermediate product of the process according to the invention.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method of hydrolysis of a peptide bond between a polypeptide sequence $R_1$ and an amino acid residue B wherein a recombinant protein represented by a formula $R_1BXJZR_3R_2$ is designed and obtained by molecular biology methods which contains, starting from the N-terminus: an amino acid sequence of a target fusion protein comprising polypeptide sequence $R_1$, a metal cation binding sequence BXJZ, and a functional domain $R_3R_2$, wherein:
   $R_1$ is a polypeptide sequence to be hydrolyzed;
   $R_2$ is a polypeptide sequence to be removed;
   $R_3$ represents a single peptide, a dipeptide, a polypeptide sequence or a covalent bond;
   B is an amino acid residue selected from the group consisting of Ser, Thr or a synthetic amino acid containing an alcohol moiety;
   X is an amino acid selected from the group consisting of Arg, Lys and His;
   J is an amino acid residue selected from the group consisting of Asp, Glu, Tyr, Met, Cys, and His, or J has a side chain bearing a group $Y_j$, wherein $Y_j$ is a salt of an inorganic acid moiety or an organic acid moiety that forms an ionic bond with a metal ion; and
   Z is an amino acid residue, occurring naturally or synthetic, containing the —NH— group, which forms a peptide bond having formula —C(O)—NH— together with amino acid residue J;
wherein the target protein $R_1$ is released by contacting the recombinant protein with a metal ion $M^{n+}$ in a buffered solution for a time and under conditions effective to achieve total hydrolysis of the peptide bond between $R_1$ and B, the metal ion $M^{+n}$ being $Ni^{2+}$; wherein the method, the sequence BXJZ does not comprise SHHK or SAHK.

2. The method of claim 1, wherein the method of creating $R_3R_2$ consists of contacting the recombinant protein, being present in a mixture of biological origin with a compound immobilized on a solid support which is capable of interacting specifically with $R_3R_2$, followed by washing off other components present in the biological mixture.

3. The method of claim 2, wherein the method is performed with the removal of the recombinant protein from the solid support, or directly on the solid support.

4. The method of claim 3, wherein $R_1$ is separated from other components using standard techniques when the method is performed in solution, while pure $R_1$ protein in solution is obtained following peptide bond hydrolysis on the solid support.

5. The method of claim 1, wherein amino acid residue X contains a side chain characterized with a large van der Waals volume.

6. The method of claim 1, wherein amino acid residue Z contains a side chain characterized with a high hydrophobicity.

7. The method of claim 5, wherein amino acid residue X is characterized with a large van der Waals volume and amino acid residue Z is characterized with a high hydrophobicity.

8. The method of claim 1, wherein the $R_1$ polypeptide sequence is a peptide or protein, $R_2$ is a peptide or protein capable of performing a specific function.

9. The method of claim 7, wherein $R_3$ comprises one, two or more amino acids that prevent an interference with an action specific to $R_2$ sequence, the action specific to $R_2$ including binding to another component or molecule.

10. The method of claim 7, wherein $R_3$ comprises one, two or more amino acids thereby preventing an inhibition of binding of metal ions to the sequence BXJZ.

11. The method of claim 7, wherein $R_2$ comprises a peptide or protein which is capable of specific binding to or interacting otherwise with another component or molecule.

12. The method of claim 1, wherein amino acid residues B, X, J, and Z are synthetic or occur naturally.

13. The method of claim 12, wherein amino acid residue J is selected from the group consisting of amino acid residues Asp, Glu, Tyr, Met, Cys, His.

14. The method of claim 12, wherein amino acid residue J is selected from the group consisting of amino acid residues Cys and His.

15. The method of claim 12, wherein amino acid residue J is His.

16. The method of claim 12, wherein amino acid residue B is selected from the group consisting of amino acid residues Ser or Thr.

17. The method of claim 12, wherein amino acid residue B is Ser.

18. The method of claim 12, wherein amino acid residue X is selected from the group consisting of amino acid residues Met, Phe, Lys, Trp, and Arg.

19. The method of claim 12, wherein amino acid residue X is selected from the group consisting of amino acid residues Lys, Trp, and Arg.

20. The method of claim 12, wherein amino acid residue X is Arg.

21. The method of claim 12, wherein Z is selected from the group consisting of amino acid residues Lys, Val, Arg, Ile, Leu, and Trp.

22. The method of claim 12, wherein amino acid residue Z is Trp.

23. The method of claim 1, wherein the buffered solution does not contain a compound which binds the metal ion $M^{n+}$.

24. The method of claim 1, wherein the buffered solution comprises Tris or Hepes.

25. The method of claim 1, wherein the hydrolysis is accelerated by including an esterase in the buffered solution.

26. The method of claim 1, further comprising modifying the C-terminal carboxyl group of the $R_1$ polypeptide sequence by reacting the carboxyl group with a compound selected from the group consisting of hydroxylamine and its derivatives, alcohols, phenols, thiols, amines, and phosphines.

27. The method of claim 1, wherein the C-terminal amino acid of the $R_1$ polypeptide forms an amide bond with amino acid residue B, and wherein the method, the $R_1$ polypeptide is purified after the hydrolysis is complete.

28. The method of claim 1, wherein $R_2$ is capable of binding to another component or molecule.

29. The method of claim 1, wherein the $R_3$ is an oligopeptide spacer sequence.

30. The method of claim 29, wherein the oligopeptide spacer sequence is at least one Ala-Pro sequence.

31. The method of claim 1, wherein the buffered solution comprises Tris or Hepes.

32. The method according to claim 1, wherein the molecular biology method is overexpression.

33. The method according to claim 1, wherein Yj is a salt of an inorganic acid moiety selected from the group consisting of a sulfate, a nitrate and a phosphate.

34. The method according to claim 1, wherein Yj is an organic acid moiety, or a salt thereof selected from a carboxylic acid, a phenol, or a thiol.

35. The method according to claim 34, wherein the organic acid moiety is a conjugate acid of an amine, a phosphine, a thioether, or an aromatic heterocyclic moiety.

36. The method according to claim 35, wherein the organic acid moiety is a protonated pyridine derivative or a protonated imidazole derivative.

37. A method of hydrolysis of a peptide bond between a polypeptide sequence $R_1$ and an amino acid residue B wherein a recombinant protein represented by a formula $R_1BXJZR_3R_2$ is designed and obtained by overexpression, which contains, starting from the N-terminus: an amino acid sequence of a target fusion protein $R_1$, a metal cation binding sequence BXJZ, and a functional domain $R_3R_2$, wherein:
  $R_1$ is a polypeptide sequence to be hydrolyzed;
  $R_2$ is a polypeptide sequence to be removed;
  $R_3$ represents a single peptide, a dipeptide, or a polypeptide sequence or a covalent bond;
  B is an amino acid residue selected from the group consisting of Ser, Thr or a synthetic amino acid containing alcoholic groups;
  X is an amino acid selected from the group consisting of Arg, Lys and His;
  J is an amino acid residue selected from the group consisting of Asp, Glu, Tyr, Met, Cys, and His, or J has a side chain bearing a group $Y_j$, wherein $Y_j$ is a salt of an inorganic acid moiety or an organic acid moiety that forms an ionic bond with a metal ion; and
  Z is an amino acid residue, occurring naturally or synthetic, containing the —NH— group, which forms a peptide bond having formula —C(O)—NH— together with amino acid residue J;
  wherein the target protein $R_1$ is released by contacting the recombinant protein with a metal ion $M^{n+}$ in a buffered solution for a time and under conditions effective to achieve total hydrolysis of the peptide bond between $R_1$ and B, the metal ion $M^{n+}$ being $Ni^{2+}$; wherein the sequence BXJZ does not comprise SHHK or SAHK, wherein the hydrolysis is carried out at near physiological conditions including a temperature range of 25-45° C. and pH 8.2.

* * * * *